(12) United States Patent
Aptekarev et al.

(10) Patent No.: US 11,793,605 B2
(45) Date of Patent: Oct. 24, 2023

(54) APPARATUS AND METHODS FOR ORTHODONTIC TREATMENT PLANNING

(71) Applicant: 3D SMILE USA, INC., Philadelphia, PA (US)

(72) Inventors: Fedor Alexandrovich Aptekarev, Moscow (RU); Sergey Leonidovich Komarinsky, Nizhniy Arkhyz (RU); Grigory Shoroshov, Krasnogorsk (RU)

(73) Assignee: 3D SMILE USA, INC., Philadelphia, PA (US)

( * ) Notice: Subject to any disclaimer, the term of this patent is extended or adjusted under 35 U.S.C. 154(b) by 532 days.

(21) Appl. No.: 16/876,546

(22) Filed: May 18, 2020

(65) Prior Publication Data

US 2021/0106403 A1    Apr. 15, 2021

(30) Foreign Application Priority Data

Oct. 15, 2019    (RU) ....... RU2019132650/14(064231)

(51) Int. Cl.
*A61C 7/00*      (2006.01)
*A61C 7/08*      (2006.01)
*G06T 7/00*      (2017.01)

(52) U.S. Cl.
CPC ............. *A61C 7/002* (2013.01); *A61C 7/08* (2013.01); *G06T 7/0014* (2013.01); *G06T 2207/20084* (2013.01); *G06T 2207/30036* (2013.01)

(58) Field of Classification Search
CPC .... A61B 6/505; G06K 9/6267; G06N 3/0454; G16H 50/20; G16H 50/70
See application file for complete search history.

(56) References Cited

U.S. PATENT DOCUMENTS 10,426,575 B1    10/2019    Raslambekov
2005/0192835 A1    9/2005    Kuo et al.
(Continued)

FOREIGN PATENT DOCUMENTS

CN    1973291 A    5/2007
CN    105769352 A    7/2016
(Continued)

OTHER PUBLICATIONS

Chinese Office Action dated Jul. 7, 2022 in Chinese Patent Application No. 201980044746.3 (with English translation), 23 pages.
(Continued)

*Primary Examiner* — Ming Wu
(74) *Attorney, Agent, or Firm* — Oblon, McClelland, Maier & Neustadt, L.L.P.

(57) ABSTRACT

The present disclosure relates to an automated process for the design of dental aligners. Specifically, the present disclosure relates to a method for generating an orthodontic treatment plan for at least one dental arch of a patient, comprising extracting control points of teeth of the at least one dental arch of the patient from received patient-related data, determining, based on the extracted control points, a target dental arch of the patient, calculating, based on the determined target dental arch of the patient, one or more teeth movement stages, and generating, by processing circuitry and based on the calculated one or more teeth movement stages, the orthodontic treatment plan for the at least one dental arch of the patient.

13 Claims, 24 Drawing Sheets

(56) References Cited

U.S. PATENT DOCUMENTS

| | | | |
|---|---|---|---|
| 2008/0085487 A1 | 4/2008 | Kuo et al. | |
| 2009/0080734 A1 | 3/2009 | Moriya et al. | |
| 2012/0171642 A1* | 7/2012 | Mehl | G06F 18/28 |
| | | | 433/223 |
| 2013/0325431 A1 | 12/2013 | See et al. | |
| 2015/0057983 A1 | 2/2015 | See et al. | |
| 2017/0128161 A1 | 5/2017 | See et al. | |
| 2017/0304023 A1 | 10/2017 | Tsai et al. | |
| 2018/0078338 A1* | 3/2018 | Way | A61C 7/00 |
| 2019/0105128 A1* | 4/2019 | Velazquez | G06T 5/002 |
| 2019/0175303 A1* | 6/2019 | Akopov | A61C 7/002 |

FOREIGN PATENT DOCUMENTS

| | | | | |
|---|---|---|---|---|
| CN | 108210095 A | | 6/2018 | |
| CN | 110025387 A | | 7/2019 | |
| CN | 110265140 A | * | 9/2019 | A61B 6/505 |
| CN | 112867461 A | | 5/2021 | |
| EP | 3 216 430 A1 | | 9/2017 | |
| RU | 2 486 875 C1 | | 7/2013 | |
| RU | 2 538 620 C1 | | 1/2015 | |
| RU | 2538620 C1 | | 1/2015 | |
| WO | WO-2012020548 A1 | * | 2/2012 | A61C 11/00 |

OTHER PUBLICATIONS

Chinese Supplemental Search Report dated Jul. 3, 2022 in Chinese Patent Application No. 201980044746.3, 2 pages.

Russian Search Report dated Oct. 15, 2019 in Russian Application No. 2019132650/14(064231), with English translation, 4 pages.

Russian Office Action dated Mar. 3, 2020 in Russian Application No. 2019132650/14(064231), with English translation, 27 pages.

Extended European Search Report dated Feb. 15, 2022 in European Patent Application No. 19934345.0, 9 pages.

Written Opinion of the International Searching Authority dated May 26, 2020 in PCT/RU2019/000890, (submitting English translation only), 3 pages.

Chinese Office Action dated Oct. 18, 2021 in Chinese Application No. 201980044746.3, with English translation, 9 pgs.

Chinese Search Report dated Oct. 11, 2021 in Application No. 2019800447463, , 1 pg.

International Search Report dated Jun. 18, 2020 in International Application No. PCT/RU 2019/000890, 1 pg.

Office Action dated Aug. 16, 2022 in Indian Patent Application No. 202117002126 (6 pgs).

Decision to Grant a Patent dated May 27, 2020 in Russian Patent Application No. 2019132650/14(064231), along with an English translation.

Office Action dated Apr. 23, 2023 in Israeli Patent Application No. 279216, and an English translation.

Office Action dated Jan. 29, 2023 in Chinese Patent Application No. 2019800447463, along with an English translation, (14 pgs.).

Office Action dated Jul. 19, 2023 in European Patent Application No. 19934345.0.

* cited by examiner

534

713

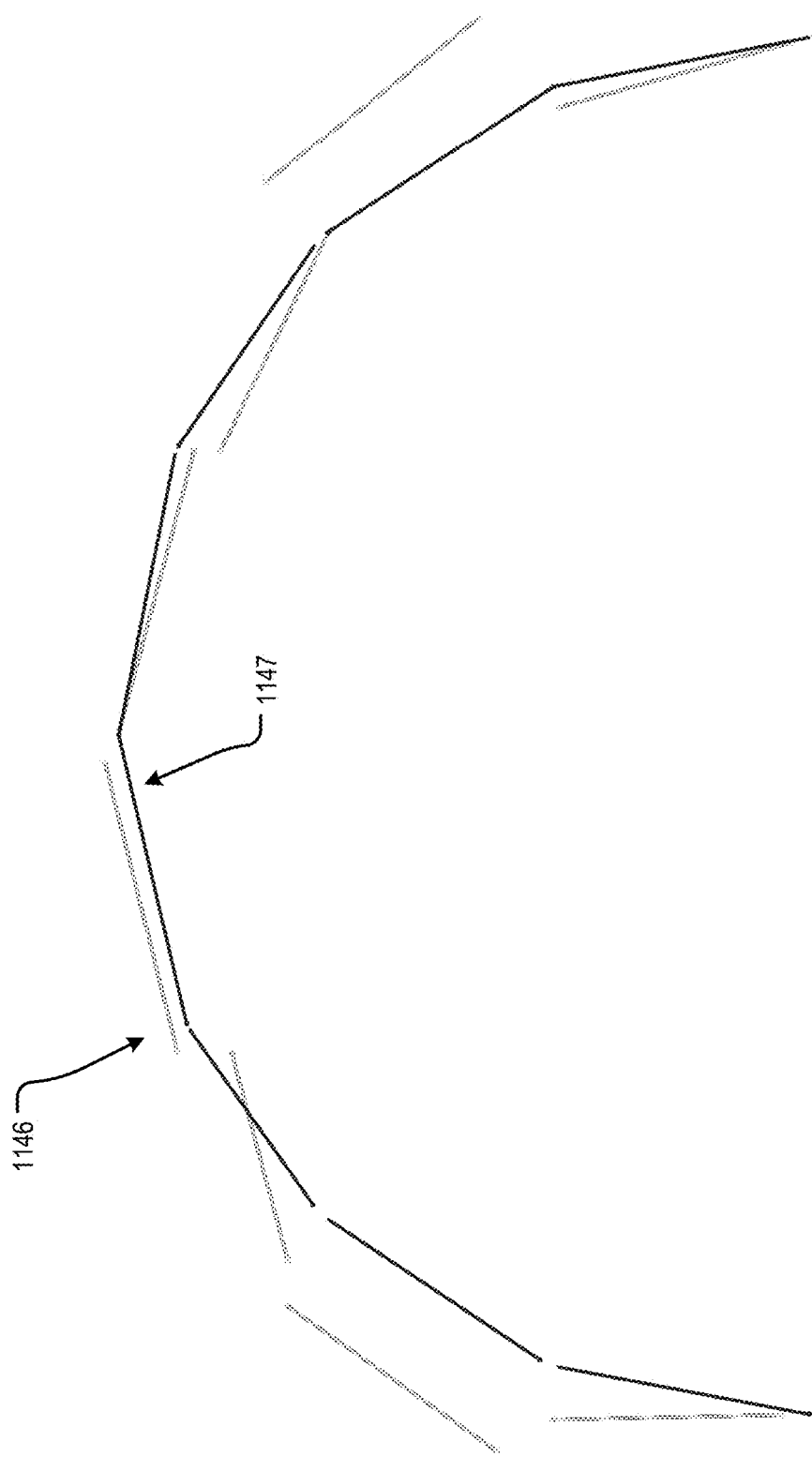

APPARATUS AND METHODS FOR ORTHODONTIC TREATMENT PLANNING

CROSS-REFERENCE TO RELATED APPLICATION

This application is based upon and claims the benefit of priority from Russian Federation Patent Application No. 2019132650/14(064231), filed on Oct. 15, 2019, the entire content of which is incorporated herein by reference.

BACKGROUND

Field of the Disclosure

The present disclosure relates to a method for the automated design of dental aligners.

Description of the Related Art

Orthodontics, generally, and dental alignment, in particular, is a well-developed area of dental care. For patients with misaligned teeth, traditional braces or, more recently, clear dental aligners, offer a strategy for improved dental function and aesthetics though graduated teeth movement. These graduated, controlled teeth movements slowly move a crown of a tooth until a desired final position is reached.

These approaches, however, often fail to appropriately consider occlusion, or contact between the upper teeth and the lower teeth, in the development of the final position of teeth of a dental arch, focusing instead on aesthetics and the mere alignment of adjacent teeth in determining the ideal crown positions. Moreover, such approaches to determining the final position of teeth of a dental arch are often laborious, requiring hours of manual attention to each tooth and to each stage of movement of the tooth.

Accordingly, an automated approach for determining a 'near-ideal' dental arch, and each intermediate position and stage required to achieve the 'near-ideal' dental arch, in view of both alignment and occlusion, has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a method, apparatus, and computer-readable medium comprising a processing circuitry configured to perform an automated process for the design of dental aligners for an orthodontic treatment.

Specifically, the present disclosure relates to a method, apparatus, and computer-readable medium comprising processing circuitry configured to perform a method for generating an orthodontic treatment plan for at least one dental arch of a patient, comprising extracting control points of teeth of the at least one dental arch of the patient from received patient-related data, determining, based on the extracted control points, a target dental arch of the patient, calculating, based on the determined target dental arch of the patient, one or more teeth movement stages, and generating, based on the calculated one or more teeth movement stages, the orthodontic treatment plan for the at least one dental arch of the patient.

The foregoing paragraph has been provided by way of general introduction, and is not intended to limit the scope of the following claims. The described embodiments, together with further advantages, will be best understood by reference to the following detailed description taken in conjunction with the accompanying drawings.

BRIEF DESCRIPTION OF THE DRAWINGS

The patent or application file contains at least one drawing executed in color. Copies of this patent or patent application publication with color drawing(s) will be provided by the office upon request and payment of the necessary fee.

A more complete appreciation of the disclosure and many of the attendant advantages thereof will be readily obtained as the same becomes better understood by reference to the following detailed description when considered in connection with the accompanying drawings, wherein:

FIG. 11 is an illustration of an initial dental arch and an ideal dental arch, according to an exemplary embodiment of the present disclosure;

DETAILED DESCRIPTION

Figure 1:
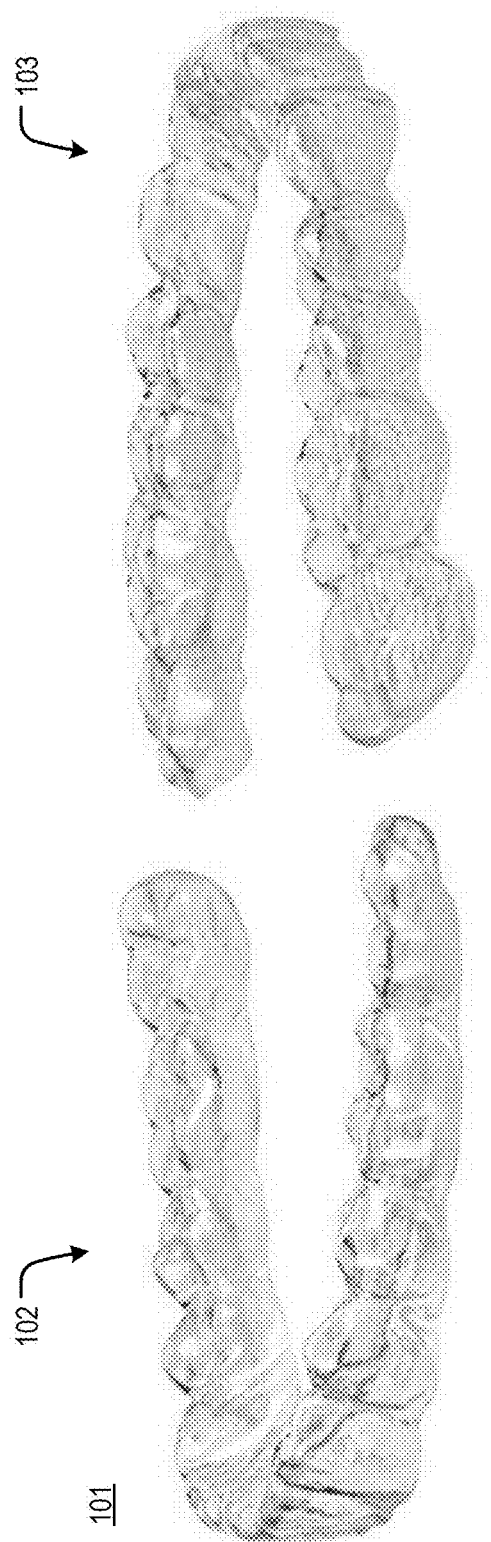
FIG. 1 is an illustration of dental aligners, according to an exemplary embodiment of the present disclosure.

The terms "a" or "an" as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases in various places throughout this specification are not necessarily all referring to the same embodiment. Furthermore, the particular features, structures, or characteristics may be combined in any suitable manner in one or more embodiments without limitation.

Occlusion, in a dental context, is the contact between teeth, either during rest when the jaw is closed or during activities in which the jaw is moving. More specifically, dental occlusion can define a relationship between teeth of the maxilla, or upper jaw bone, and teeth of the mandible, or lower jaw bone, when they are in or near contact.

Moreover, dental occlusion can be predominately separated into occlusion of the molars and occlusion of the canines. When describing the relationship between, for instance, molars of the upper dental arch and molars of the lower dental arch, three classes may be used to discern proper occlusion from improper occlusion. In an example, occlusion of the mesiobuccal cusp of the upper first molar (i.e., maxillary first molar) with the buccal groove of the lower first molar (i.e., mandibular first molar) can be classified as Class I. Posterior occlusion of the mesiobuccal cusp of the maxillary first molar relative to the buccal groove of the mandibular first molar can be classified as Class III. Such classifications play an important role in diagnosis of and treatment planning for dental health. To this end, Class I occlusion can be used to define an acceptable occlusion, while Class II and Class III can be used to define malocclusion that may necessitate medical intervention, surgical or otherwise. In fact, failure to maintain or restore proper occlusion, even when proper alignment may be present, may result in patient discomfort and pain resulting from excessive wearing of the teeth, fractures of the teeth, and/or cracks of the teeth that become more frequent with malocclusion.

In other words, a goal of orthodontic treatment should be to ensure proper occlusion. This means that orthodontic treatment planning involves not just intra-arch dental alignment but also inter-arch functional relationships that define proper dental contact between the upper dental arch and the lower dental arch. Therefore, treatment planning that focuses solely on alignment of simplified objects (e.g., spheres or other primitive shapes) within a dental arch should be cautiously applied in clinical practice as the risk of malocclusion is unacceptably high despite the fact that the 'objects', or teeth, themselves are aesthetically aligned.

As noted above, however, traditional approaches to orthodontic planning, in part stymied by the burden of manual treatment planning, have focused predominantly on alignment of adjacent teeth within a single dental arch (i.e., arches of the mandible or the maxilla, separately). Considering the above-described importance of occlusion in dental health, it can be appreciated that any system hoping to provide effective orthodontic treatment planning must fully consider inter-arch functional relationships between teeth.

Accordingly, the present disclosure describes an automated system for orthodontic treatment planning that considers one or both of alignment and occlusion in determining an ideal arch and determining the movements necessary to move each dental arch to a target position.

According to an embodiment, an orthodontic treatment planning system (OTPS) of the present disclosure can include processing circuitry for executing processes thereof. The processing circuitry or processing circuitries may be realized in a module or one or more modules. In an example, the OTPS can include one or more modules for the creation, uploading and preliminary processing of three-dimensional models of teeth of a patient with consideration to prescriptions, rules, and the like. For instance, the OTPS can include a module for determining an alignment-based ideal dental arch, a module for determining an occlusion-based ideal dental arch, a module for locating dental control points for use in determining the occlusion-based ideal dental arch, and a module for designing a treatment based on dentition, prior prescriptions, orthodontic rules, and treatment history. Determination of the occlusion-based ideal dental arch can include optimization of the target dental arch in view of prescriptive and orthodontic rules and with controls for collisions of teeth during the determined teeth movements.

According to an embodiment, the OTPS may also include a module for determining dental features of each dental arch of a patient, the dental features including local axes of each tooth's coordinates. In complicated cases of worn teeth, described in detail in subsequent figures, the OTPS can perform a method for automatic correction of dental features of the dental arch, local axes, and the like. For instance, a worn tooth can be approximated by a machine-learning algorithm trained on a database of healthy teeth, the identifiable dental features of each of the healthy teeth being virtually used to position and move a worn tooth. Alternatively, via visualization methods performed by the OTPS, dental features can be edited manually in order to generate the occlusion-based ideal dental arch.

According to an embodiment, an occlusion-based ideal dental arch may be a 'near-ideal', or target, dental arch, as an exactly ideal dental arch may not be possible. In an example, a number of possible combinations of teeth positions that satisfy a threshold for a dental arch may be generated and considered. The best dental arch, by comparison, can be selected as the target dental arch.

According to an embodiment, the target dental arch may not be achievable in a single teeth movement, or stage of tooth movement. In some cases, it may be necessary to perform a plurality of teeth movements, or stages of tooth movement, in order to move teeth from an initial position to a final position corresponding to the target dental arch. For instance, 'collisions' and orthodontic rules, among others, may prohibit two adjacent teeth from moving to a final position simultaneously, thereby necessitating at least a first stage wherein a first tooth is moved and at least a second stage wherein a second tooth is moved. Additional rules may define that four adjacent teeth may not be simultaneously moved, for instance, necessitating movements of pairs of teeth or individual teeth as appropriate to satisfy a target position. Moreover, each stage, whether one or more, can be determined with further consideration to clinical constraints and the like, as will be described in greater detail with reference to subsequent figures. As a simplified example of an exemplary case of such clinical constraint, it may be prescribed that a single stage cannot result in a movement of a tooth of more than 250 microns. Therefore, if a total required movement of a tooth is 750 microns, the respective movement would require at least 3 stages of teeth movement.

In view of the above, and in a simplification of an exemplary embodiment of the present disclosure, orthodontic rules may prohibit concurrent movement of anterior teeth of a mouth and posterior teeth of the mouth. In this example, a combination of the necessitated stages of teeth movement may be considered, generally, as 'phases' of teeth movement. For instance, it can be determined at the outset that more than one phase of teeth movement, each phase of teeth movement comprising a series of stages of teeth movement, may be needed in order to move a dental arch from an initial position to a final position corresponding to a target dental arch. In the case wherein anterior teeth and posterior teeth must be moved independently, the combination of stages required to move anterior teeth of a mouth may be considered to be an 'anterior phase' of teeth movement and the stages required to move posterior teeth of the mouth may be considered to be a 'posterior phase' of teeth movement. As will be described with reference to subsequent figures, the OTPS determines, at the outset, a number of phases of teeth movement, each phase of teeth movement representing an intermediary position, or de facto target position, of each tooth. Therefore, for each phase and respective intermediary position, stages of teeth movements can be determined with consideration of all possible variables and constraints, orthodontic, clinical, and otherwise.

According to an embodiment, data inputs to the OTPS can include digital models of dentition of a patient, prescription and treatment history, orthodontic rules, and controlled parameters. Such orthodontic rules and clinical constraints may include qualitative constraints defining the number and types of teeth that may be moved simultaneously or quantitative constraints defining the amount of acceptable movement.

According to an embodiment, a result of the OTPS may be the planning of teeth movements towards a patient's determined target dental arch. To this end, the OTPS can execute a method of generating a series of teeth movements that move teeth of a dental arch towards the target dental arch. The teeth movements, or phases of teeth movement, can be divided into stages, each stage thereof defining and providing a 'template' for an orthodontic treatment device, such as the dental aligners of FIG. 1. Orthodontic treatment devices can be developed for each of the one or more stages of teeth movement. In an example, each stage is optimized by the OTPS according to prescriptions, orthodontic rules, and clinical constraints, accounting for possible collisions and clashes based on a digital dentition model of the patient.

According to an embodiment and as indicated above, positions of teeth in the determined target dental arch may require one or more phases of teeth movement. In an example, the position of each tooth at each of the one or more phases can be considered an intermediate position. Accordingly, specific calculations of tooth trajectories corresponding to stages of movement, such as those described in FIG. 14, can be performed in view of the intermediate position and/or the determined target dental arch, as the intermediate position may become a de facto target position.

As suggested, the OTPS can include all of the necessary rules established on the basis of the medical record of the patient and as required for the design of the teeth movement protocols. The stages of teeth movements within each phase of teeth movement can be monitored within the OTPS.

According to an embodiment, the OTPS can include a module for the generation of each stage of teeth movement. Each stage of teeth movement can be accompanied by a three-dimensional model generated in accordance with each teeth movement, the three-dimensional model defining an orthodontic treatment device.

According to an embodiment, the OTPS can include one or more modules for visualization of dentition of the patient and the process of teeth movements towards the near-ideal dental arch.

According to an embodiment, and as noted above, during complicated cases when teeth of a patient are worn and cusps and incisal edges or incisal ridges are not easily identifiable, the OTPS may provide automatic or semi-automatic correction for worn features and identification of dental control points therefrom. Automatic or semi-automatic correction for worn features and identification of dental control points therefrom can include incorporation of machine-learning based techniques, the dental control points being identified by application of a machine-learning based approach that is trained on a database of unworn teeth.

These dental control points can then be used to generate an ideal dental arch or target dental arch.

According to an embodiment, the processing circuitry of the OTPS can be located at one or more of a local device, a cloud-based device, or a combination thereof.

According to an embodiment, the present disclosure describes a system for generating patient-specific orthodontic treatment devices.

With reference now to the figures, FIG. 1 is an illustration of dental aligners created for a stage of teeth movement and based on a prescription of an orthodontic treatment plan generated by the OTPS, according to an embodiment of the present disclosure. In an embodiment of the present disclosure, dental aligners 101 can be generated for each determined stage of the orthodontic treatment, the dental aligners 101 gradually repositioning each tooth of a dental arch. To this end, the dental aligners 101 may be a dental aligner for an upper dental arch 102 and a dental aligner for a lower dental arch 103, the dental aligners 101 being configured to provide proper alignment and occlusion of the upper dental arch 102 and the lower dental arch 103 in a target position.

Figure 2:
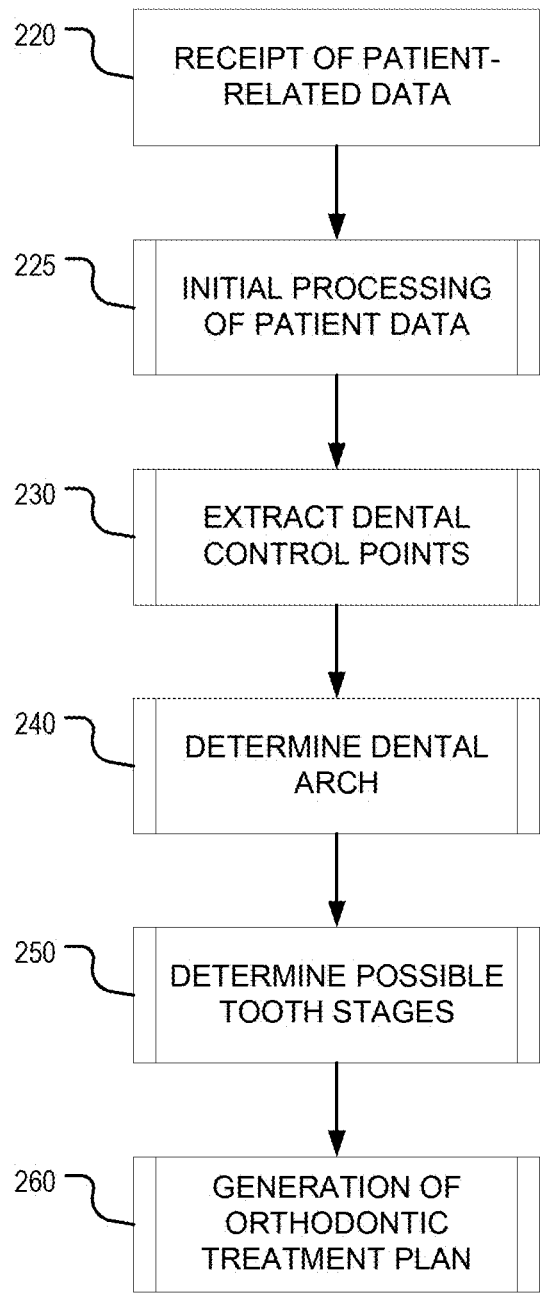
FIG. 2 is a flow diagram of a process of an orthodontic treatment planning system, according to an exemplary embodiment of the present disclosure.

FIG. 2 is a flow diagram of a process 200 of the OTPS, according to an exemplary embodiment of the present disclosure. Each step of the process 200 of the OTPS can be performed by local and/or remote processing circuitry.

Initially, at step 220 of process 200, patient-related data can be received. Such patient-related data, discussed in more detail in FIG. 3, can include medical prescriptions from doctors as well as medical images and orthodontic rules that, in part, define the prescription.

At sub process 225 of process 200, the received patient-related data can be initially processed. Such initial processing can include, for instance, generation and analysis of a three-dimensional model of dentition of a patient generated from the received medical images. In order to ensure the three-dimensional model is of suitable accuracy for establishing dental control points and generating a useful orthodontic treatment plan, sub process 225 can include manipulation of the generated three-dimensional models, including smoothing of features, decimation interpolation, and similar strategies for creating a complete data set of the model. Further to the above, teeth identification and assignation can be roughly determined via image recognition techniques known in the art. In this way, incisors, canines, premolars, or bicuspids, molars, and the like of the maxillary dental arch and the mandibular dental arch can be appropriately classified, or labeled, for subsequent processing. In an embodiment, the labeling and assigning of the teeth of the dental arches can be performed manually or automatically in accordance with a specified list. Additionally, parameters of the three-dimensional model can be modified in accordance with the orthodontic data of the patient. For instance, the orthodontic data of the patient can include specific instructions from a doctor and/or can be based on the anatomy of the patient, the orthodontic data instructing movement of a specific tooth. In an example, such movement instruction of the specific tooth can be that the specific tooth is prevented from moving.

According to an embodiment, initial processing of sub system 225 of process 200 can include recognition of and accommodation for missing teeth. For example, if tooth number 2 (i.e. the second furthest tooth on the right hand side of the maxillary dental arch) is missing, the sub system 225 of process 200 can generate a model of a crown of a 'standard' tooth number 2 to replace the missing tooth number 2. In replacing the missing teeth with a virtual crown of the missing tooth, the OTPS can consider a complete dental arch in determining teeth movements.

Figure 4:
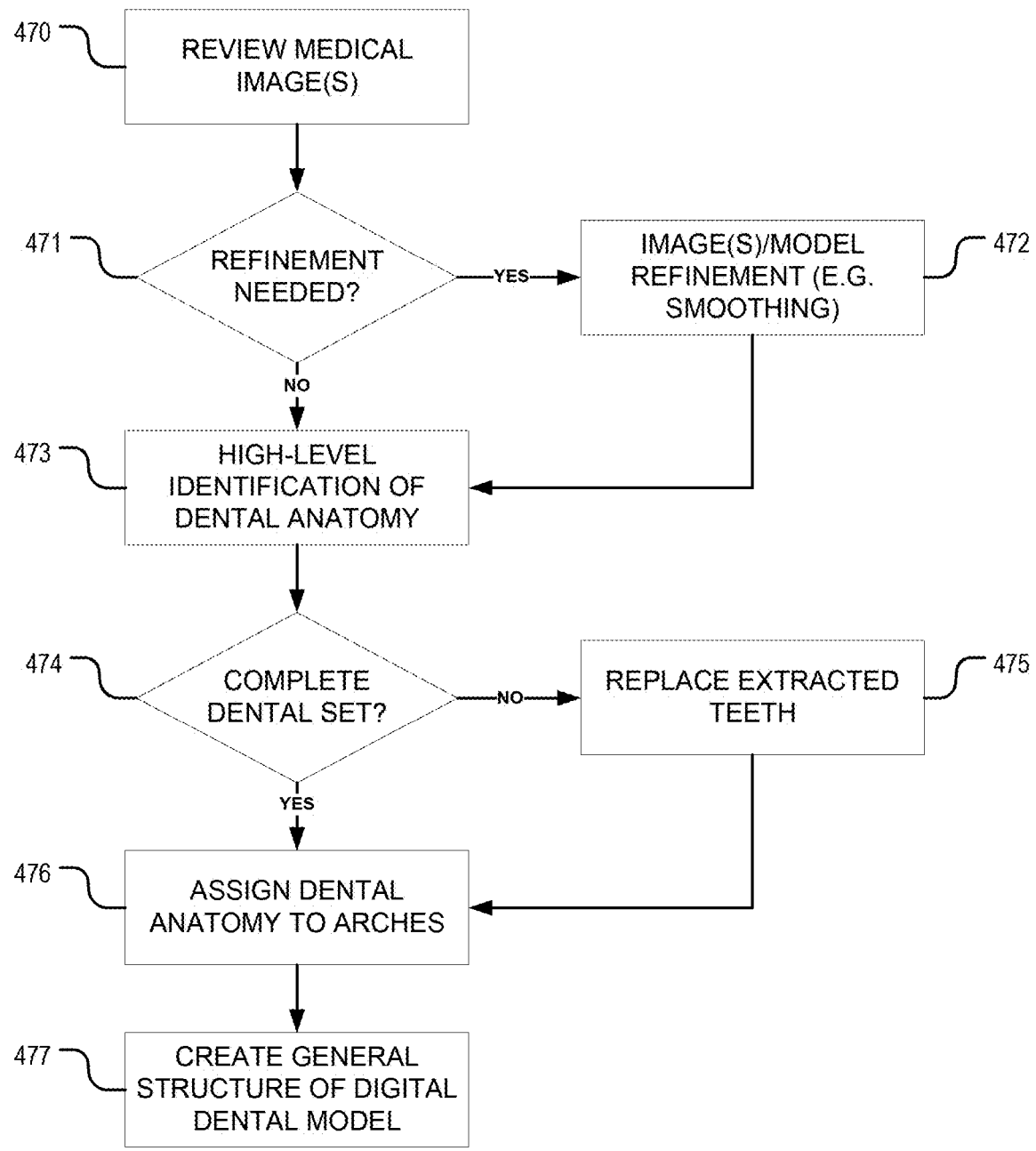
FIG. 4 is a flow diagram of a sub process of a process of an orthodontic treatment planning system, according to an exemplary embodiment of the present disclosure.

A more detailed description of sub process 225 of process 200 will be described with respect to FIG. 4.

At sub process 230 of process 200, dental control points of each tooth within the three-dimensional model can be extracted in order to generate a refined model of the tooth in view of dental alignment and occlusion. As will be described in more detail with respect to FIGS. 5A through 9B, the dental control points may be, in an example, dental features of each tooth including cutting edges such as incisal ridges, or incisal edges, of incisors, cusps of canines, cusps of premolars and molars, and the like. In determining the dental features, a three-dimensional model of each tooth is generated and processed in order to determine and generate local axes for each tooth within the three-dimensional model. In the case of complicated prescriptions, dental features can be visualized and edited automatically, semi-automatically or manually. In an example, semi-automatic editing can include, in an instance, manual selection of a dental feature to be modified and automatic correction thereof, or, in another instance, automatic identification of a dental feature to be modified and manual correction thereof. Automatic identification, as part of semi-automatic correction, of the dental feature to be modified may be based upon a comparison of a parameter of the dental feature to a threshold value of the parameter. It can be appreciated, however, that the above-described cases are merely exemplary and other cases may be considered without deviating from the spirit of the invention.

At sub process 240 of process 200, the extracted dental control points can be used to determine an ideal dental arch for the upper dental arch and for the lower dental arch in view of alignment and occlusion. In cases when an ideal dental arch is not possible, a 'near-ideal' dental arch, or target dental arch, can be identified according to a sub process described in more detail with reference to FIG. 10. As an example, an ideal dental arch can be determined as a dental arch that is achieved without dental collisions (e.g. collisions and/or clashes) of neighboring teeth. However, in a clinical case, it may be impossible for each tooth to reach an ideal dental arch position while avoiding dental collisions. Such dental collisions can be determined by the OTPS and can be accounted for in developing a target dental arch, the target dental arch being selected from a set of determined dental arches having a series of possible tooth movements and final arrangements that achieve a 'near-ideal' dental arch. In an embodiment, a target dental arch can include an expansion of a dental arch in the process of accounting for, or avoiding, dental collisions. For instance, the expansion of the dental arch can be a target final position or can be implemented as an intermediate position in order to avoid collisions, the intermediate position being a phase defined by one or more stages of teeth movement.

At sub process 250 of process 200, possible teeth phases and stages of teeth movement thereof are determined based upon the determined target dental arch of sub process 240. Following a determination of a target dental arch and final positions of teeth thereof, and in view of an initial position of each tooth of the dental arch, target intermediary teeth positions can be determined. The target intermediary teeth positions may represent, in an example, phases of teeth movement, each phase being defined by stages of teeth movement that allow the target intermediary teeth positions to be achieved. In an example, a qualitative comparison of the initial positions of teeth and the corresponding final positions of teeth of the determined target dental arch, in view of orthodontic constraints and clinical constraints, can be made to aid in determining the target intermediary teeth positions and, thus, the number of phases required to achieve the final position of the determined target dental arch. Moreover, stages of teeth movement required to achieve the target intermediary teeth positions can be defined in view of orthodontic constraints, clinical constraints, and other patient-related data 220. For example, a positional difference, for instance, between the final positions of teeth of the target intermediary teeth positions of each phase and the initial positions of corresponding teeth, in view of movement constraints, can inform the number of stages of teeth movement required.

As described in detail with reference to FIGS. 14 and 15, the generation of possible teeth movements, or possible teeth trajectories, for each teeth movement phase can include the generation of a list of possible paths (i.e. tree of teeth movements) which may achieve the target intermediary teeth positions of the target dental arch in view of route length, speed of movement, possible collisions and clashes, and orthodontic rules. In an example, the list of possible paths may include multiple possible movement paths wherein a trajectory, or vector, of each path reflects a single stage of movement. In another example, the list of possible paths may include multiple possible movement paths wherein each movement path includes multiple trajectories, or vectors, reflecting multiple stages of movement needed in order to achieve the target intermediary teeth position. As indicated, each list of possible paths can include a plurality of movement paths defined by stages needed in order to satisfy each phase of teeth movements. Accordingly, this list of possible paths, and teeth movement stages therein, can be provided to sub process 260 of process 200.

At sub process 260 of process 200, an optimal path can be selected, with possible review by a medical professional, as a set of teeth movement stages that define an orthodontic treatment plan. The orthodontic treatment plan can include a prescription, or guidance, of the optimal path for each phase of treatment. Accordingly, the prescription of the orthodontic treatment plan can be used to guide fabrication of corresponding dental aligners, such as those in FIG. 1, or similar bracing device. Sub process 260 will be described in more detail with reference to FIG. 16A and FIG. 16B.

Process 200, introduced above, will now be described in detail with reference to subsequent figures.

Figure 3:
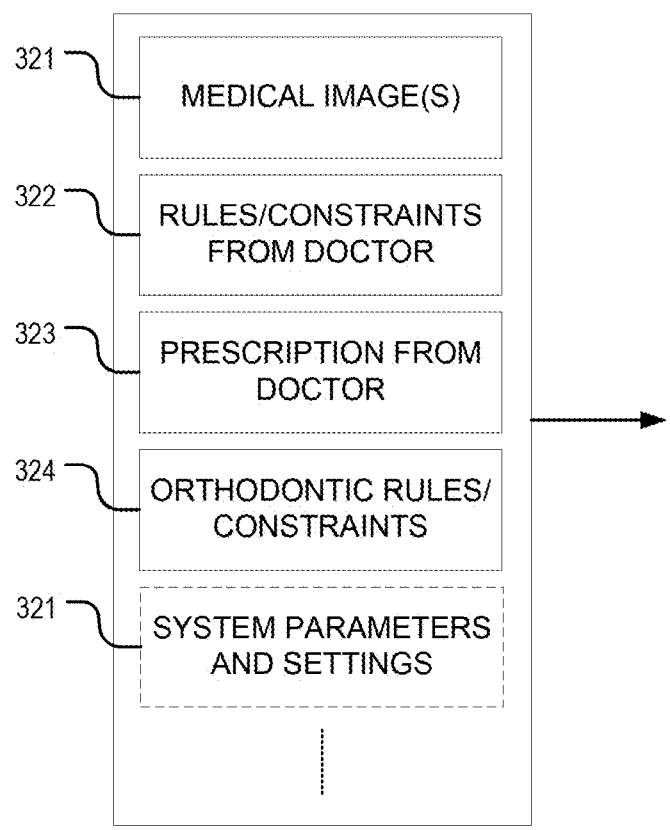
FIG. 3 is an illustration describing patient-related data of an orthodontic treatment planning system, according to an exemplary embodiment of the present disclosure.

With reference now to FIG. 3, step 220 of process 200 of the OTPS includes receipt of patient-related data. The patient-related data can include, inter alia, one or more medical images 321, rules and constraints from a doctor 322, a dental prescription from the doctor 323, orthodontic rules and constraints 324, and system parameters and settings 321, the system parameters and settings 321 being, in an example, related to the one or more medical images 321. The rules and constraints from the doctor 322 can include, among others, "do not move teeth 9, 10, and 11 as they form a bridge" or "do not close space between teeth 13 and 14 as this space is or will be occupied by an implant". The dental prescription from the doctor 323 can include "treat both dental arches", "expand upper dental arch", "narrow lower dental arch", "reduce overjet", "improve midine", "do not move teeth 7 through 13", "add posterior expansions", "level incisal edges", and the like. The orthodontic rules and constraints 324, which may be defined according to known orthodontic standards and general guidelines, can be, as an example, a limitation that a maximum movement distance allowed for a tooth within one stage of teeth movement is 250 microns.

The one or more medical images 321 received at step 220 of process 200 may be acquired by a variety of modalities. However, it should be appreciated that digital representations and/or three-dimensional models of dentition of a patient demand highly resolved data, as the characteristic teeth size and possible magnitude of teeth movements are sufficiently small. Such accuracy and precision can be required to extract dental features, account for clashes, and generate teeth movements in subsequent steps of process 200. Therefore, an imaging modality must be correspondingly accurate and precise. To this end, modalities used to acquire digital representations of an initial position of dentition of a patient can include, as non-limiting examples, impressions, intraoral scan, ultrasound, X-rays, computed tomography, and magnetic resonance imaging, used individually or in combination.

According to an embodiment, in order to create a digital representation and/or three-dimensional model of dentition of a patient, an intraoral scanner may be employed to acquire topographical characteristics of crowns of teeth. The intraoral scanner may employ a modality selected from a group including but not limited to lasers, infrared light, and structured light. So that teeth movements can be determined in the context of the crowns of the teeth and, for instance, the roots of the teeth (described later), a radiographic imaging modality may be employed in order to acquire spatial information relating to the roots and periodontal tissues, including soft tissues and hard tissues (e.g. alveolar process) thereof. Such technique(s), discussed later in the present disclosure, is described in U.S. patent application Ser. No. 16/017,687, incorporated herein by reference in its entirety. In an embodiment, the radiographic imaging modality may be selected from a group including but not limited to projection radiography, computed tomography, dual energy X-ray absorptiometry, fluoroscopy, and contrast radiography. In an example, the radiographic imaging modality may be cone beam computed tomography. Radiographic images may comprise multi-planar radiographic images including but not limited to sagittal, transverse, and coronal. It should be appreciated that, apart from radiographic techniques, a variety of imaging modalities including but not limited to ultrasound may be used for acquisition of images describing spatial information of the roots and periodontal tissues.

In an embodiment, rules and constraints from a doctor 322 may include diagnosis and treatment recommendations that can be considered by the OTPS during treatment planning, the diagnosis and treatment recommendations including all of the data and evaluations required by the system such as the index of the complexity of the pathology, potential restrictions, and other specialized data.

In an embodiment, a prescription from a doctor 323 can include general instructions given by a doctor when other patient-related data is submitted. Such instructions can include constraints set by clinical protocols of tooth movement that define how many teeth can be moved simultaneously, the maximum distance that the teeth can be moved, the speed at which teeth may be moved, the types of movement that require external devices (i.e. attachments), and what types of movement can be combined. Clinical protocols of tooth movement can be updated according to clinical results.

Having received the patient-related data at step 220 of process 200, initial processing can be performed. Accordingly, and with reference to FIG. 4, a flow diagram of sub process 225 of process 200 of the OTPS, according to an exemplary embodiment of the present disclosure, will be described.

At step 470 of sub process 225, the one or more medical images received at step 220 of process 200 can be reviewed.

Such review can include evaluating the one or more medical images in two-dimensions or evaluating three-dimensional digital models generated from the received one or more medical images to identify data therein that may be of insufficient quality for subsequent analysis and treatment planning. For instance, a specific region of a medical image, plurality of medical images, or digital model may be of limited pixel density and, accordingly, may not provide sufficient data for subsequent processing. In another instance, a specific region of a medical image(s) or digital model may be lacking entirely, accidentally missed during acquisition of the medical image(s).

If, at step 471 of sub process 225, it is determined that refinement of at least one of the one or more medical images or digital model is not required, the sub process 225 may continue to step 473. If, however, it is determined that refinement of at least one of the one or more medical images or digital model is needed, refinement can be performed at step 472 of sub process 225. For instance, the missing data can be replaced by an estimation of the missing data, the estimation being based on simple geometric models or more complex machine learning-based approaches that estimate the missing data according to an atlas of medical images of 'normal' dentition and two-dimensional representations or three-dimensional digital models generated therefrom. Accordingly, the refinement may be smoothing, decimation interpolation, and the like, performed on two-dimensional data of each of the one or more medical images, three-dimensional data of each digital model, or a combination thereof. It can be appreciated that additional refinement strategies, including but not limited to three-dimensional model parameterization or re-parameterization, may be used without deviating from the spirit of the invention.

At step 473 of sub process 225, high-level identification of dentition, and dental anatomy, specifically, can be performed. The high-level identification can include image recognition of dental structures, including the teeth, and classifying, or labeling, of each tooth according to a selected nomenclature. It can be appreciated that a variety of methods for identifying and labeling dental anatomy may be implemented, as would be understood by one of ordinary skill in the art. In an example, each tooth of the recognized teeth can be labeled according to the Universal Numbering System, wherein tooth number 1 is the tooth farthest back on the right hand side of the mouth in the upper dental arch and tooth number 17 is the tooth farthest back on the left hand side of the mouth in the lower dental arch. Notably, labeling the recognized teeth according to the Universal Numbering System allows for the identification of missing teeth in certain patients, as the Universal Numbering System labels each tooth according to expected dentition of a 'control' or healthy patient, skipping missing teeth, when appropriate.

Because of this, and as introduced above, missing teeth can be identified at step 474 of sub process 225. In particular, the labeled one or more medical images and/or digital model can be evaluated to determine if a complete dental set is available. If it is determined that a complete dental set exist, each labeled tooth can be 'assigned' to the upper dental arch or the lower dental arch at step 476 of sub process 225. If, however, teeth are determined to be missing, a result, for example, of extraction by a previous dental operation, the teeth can be 'replaced' at step 475 of sub process 225. 'Replacing' the tooth can include inserting a virtual crown in place of the missing tooth, the virtual crown being a normative tooth crown selected from an atlas of dental arches or, alternatively, an output of a machine learning-based approach that considers patient-specific factors in developing the shape of the tooth crown. Having 'replaced' the missing teeth, sub process 225 can proceed to step 476, wherein each labeled tooth can be assigned to either the upper dental arch or the lower dental arch, thereby allowing for subsequent determinations of occlusion.

At step 477 of sub process 225, a general structure of a digital dental model can be generated from the labeled and assigned dental anatomy of the patient, creating a holistic three-dimensional digital model of the dental environment. This digital dental model can be used in subsequent sub processes as an 'initial model' of dentition of the patient, the initial model being used as the basis for identifying an ideal dental arch, target dental arch, and for determining teeth movement paths and trajectories of each teeth movement stage therein.

Briefly returning to FIG. 2 and having performed initial processing of patient data at sub process 225, process 200 proceeds to sub process 230, wherein dental control points are extracted. Dental control points, such as ridges, cusps, and incisal edges, allow for the accurate determination of alignment and occlusion via, at least, dental features and contact points and, therefore, must be determined in order to generate an ideal dental arch, a target dental arch, and teeth movement paths thereto.

As is understood in general mathematics, a 'control point' can be understood to be a control point of a curve. Similarly, as described in the present disclosure, a 'dental control point' of a tooth of a dental arch can be, among others, a contact point, and an ideal dental arch can be represented by a curve designed from a polyline whose sections are inner intervals between contact points of neighboring teeth of a dental arch. Therefore, as described in FIG. 5A through 9B, extraction of dental control points, including contact points, is necessary for identification of the ideal dental arch.

Dental control point extraction can be performed by a variety of methods, including via the use of isolines, neural networks, image recognition, and the like. It can be appreciated that the dental control points described herein are merely exemplary of a variety of dental control points that may be used for the same purpose without deviating from the spirit of the invention of the present disclosure. The use of isolines, specifically, for dental control point extraction, will be described, initially, with reference to sub process 230 of FIG. 5A.

Figure 6:
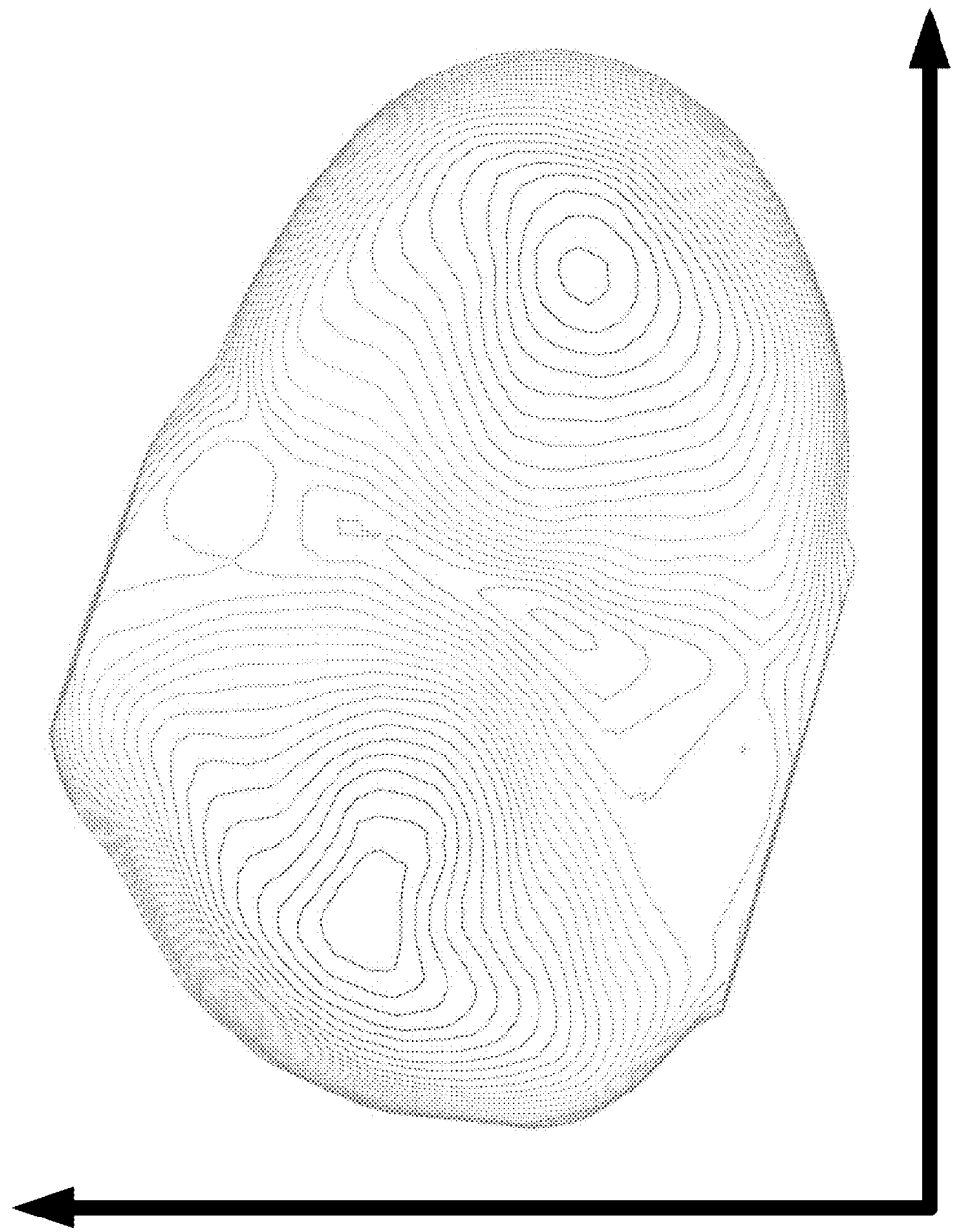
FIG. 6 is an illustration of a two-dimensional representation of isolines determined by a sub process of a process of an orthodontic treatment planning system, according to an exemplary embodiment of the present disclosure.
Figure 7A:
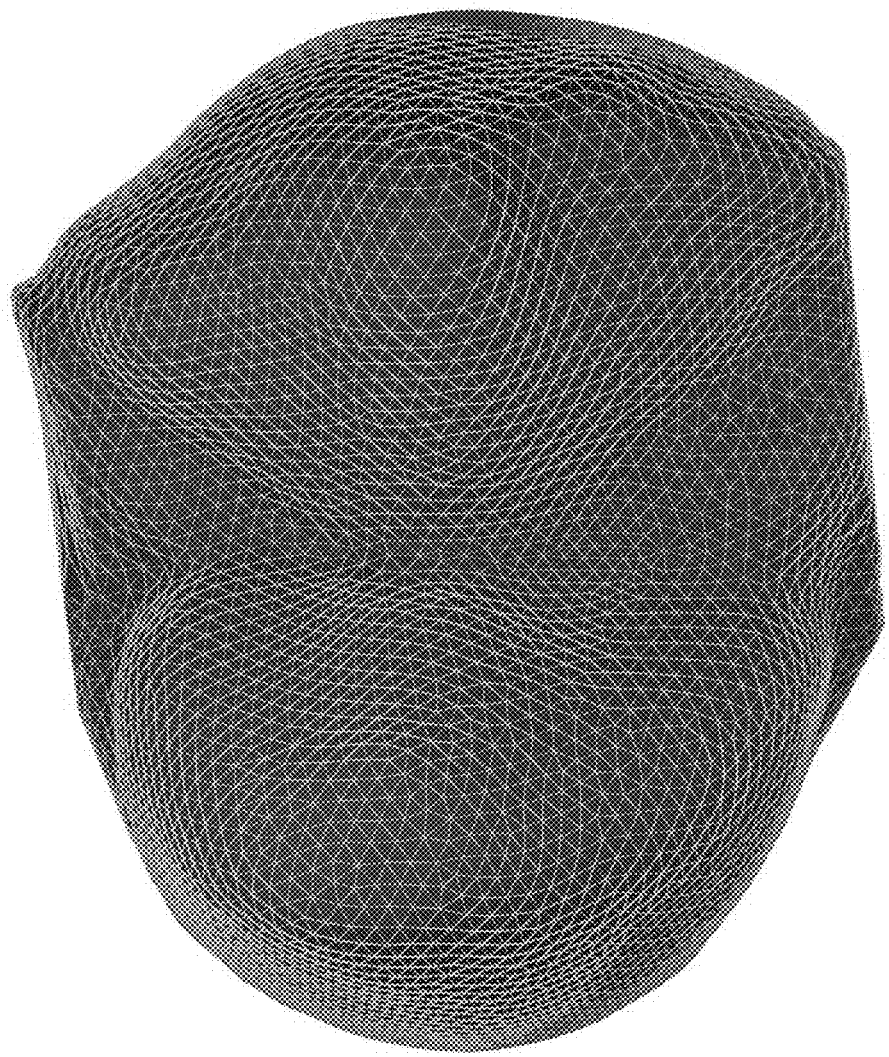
FIG. 7A is an illustration of dental feature identification in a three-dimensional rendering of a tooth, according to an exemplary embodiment of the present disclosure.
Figure 7B:
FIG. 7B is an illustration of dental feature identification in a three-dimensional rendering of a tooth, according to an exemplary embodiment of the present disclosure.
Figure 7C:
FIG. 7C is an illustration of dental feature identification in a three-dimensional rendering of a tooth, according to an exemplary embodiment of the present disclosure.
Figure 7D:
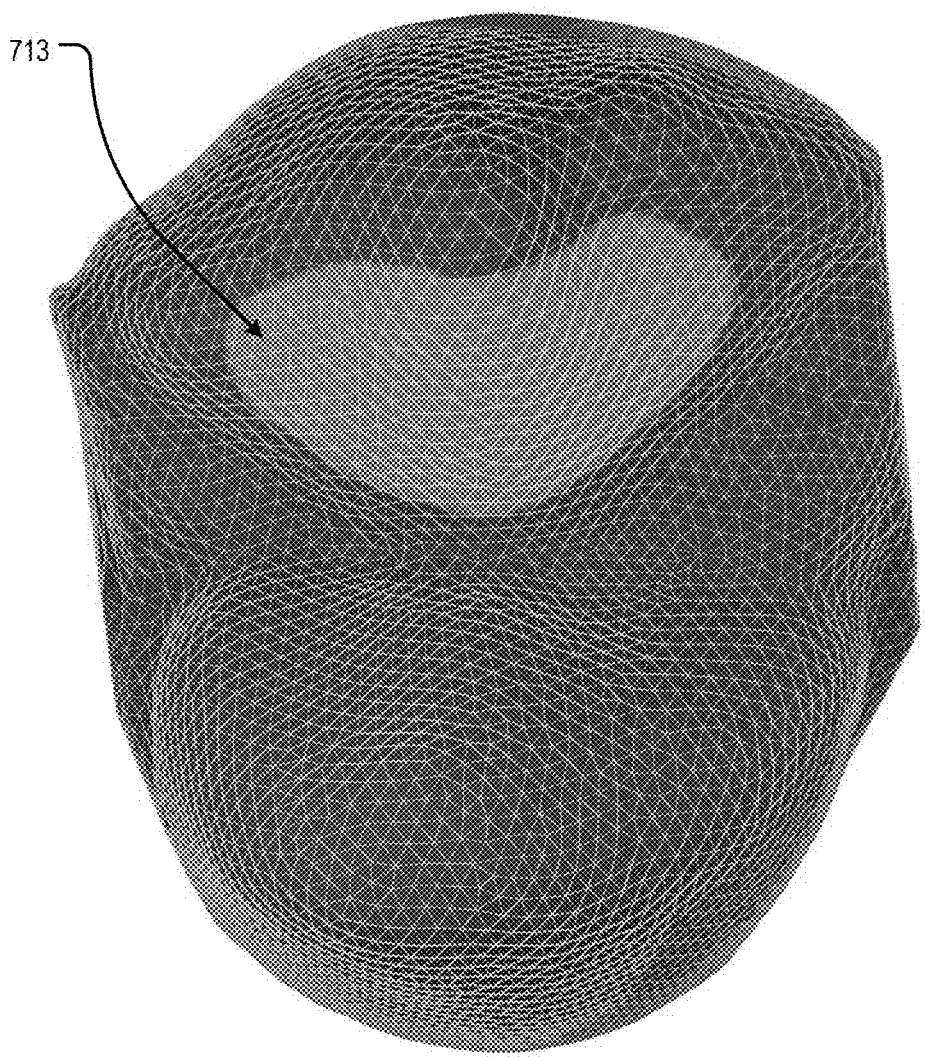
FIG. 7D is an illustration of dental feature identification in a three-dimensional rendering of a tooth, according to an exemplary embodiment of the present disclosure.
Figure 7E:
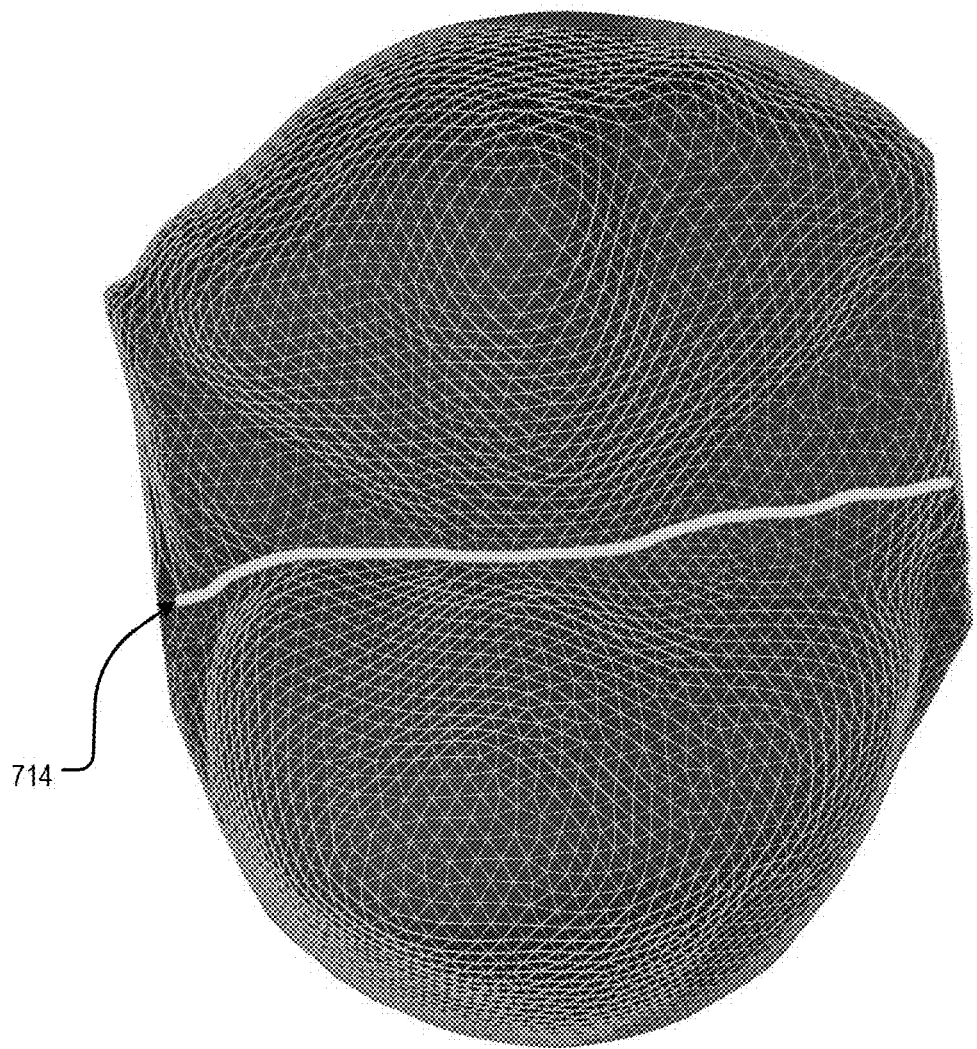
FIG. 7E is an illustration of dental feature identification in a three-dimensional rendering of a tooth, according to an exemplary embodiment of the present disclosure.
Figures 8A, 8B:
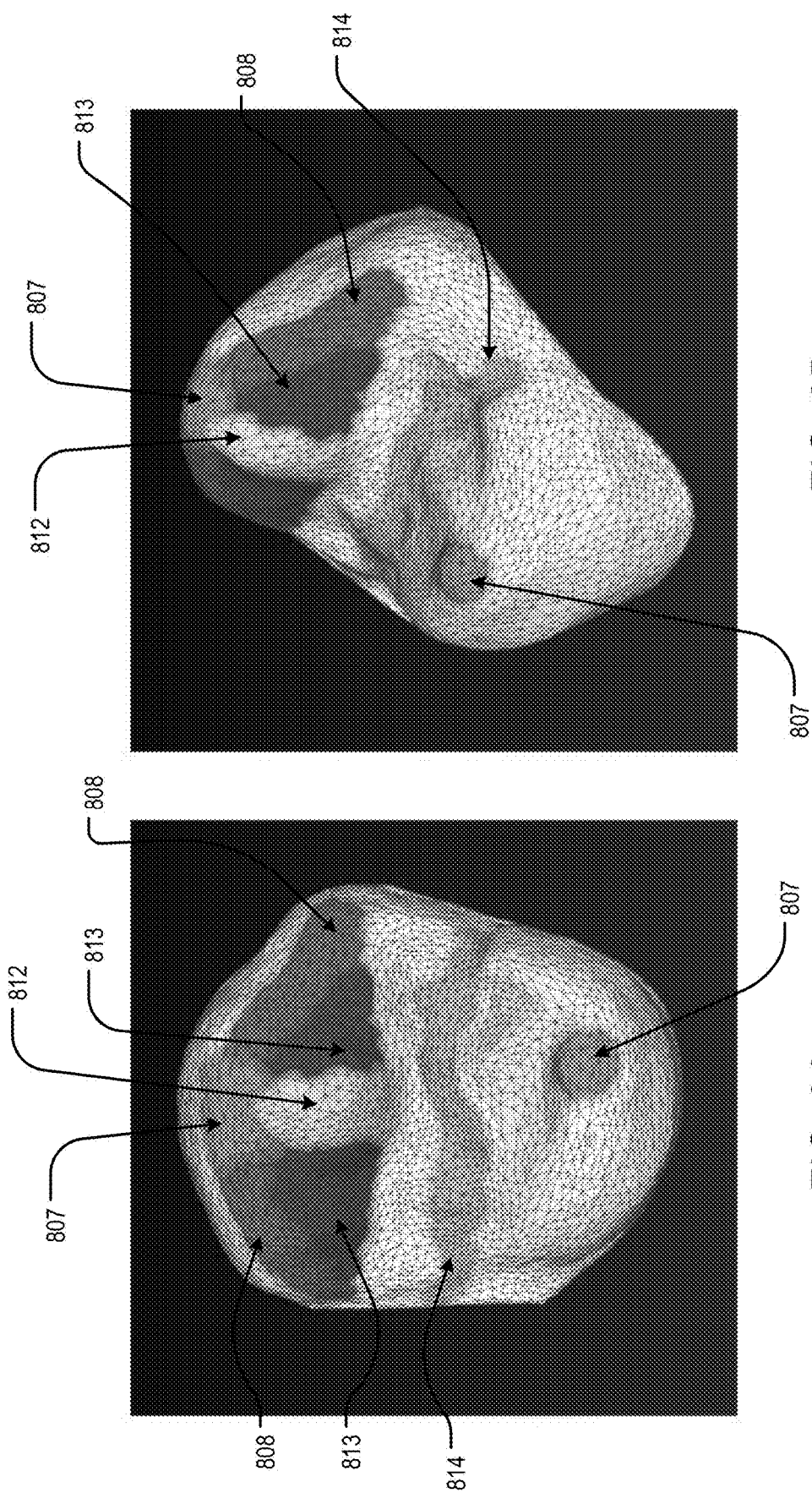
FIG. 8A is an illustration of neural network-based dental feature identification in a three-dimensional rendering of a tooth, according to an exemplary embodiment of the present disclosure.
FIG. 8B is an illustration of neural network-based dental feature identification in a three-dimensional rendering of a tooth, according to an exemplary embodiment of the present disclosure.
Figure 9B:
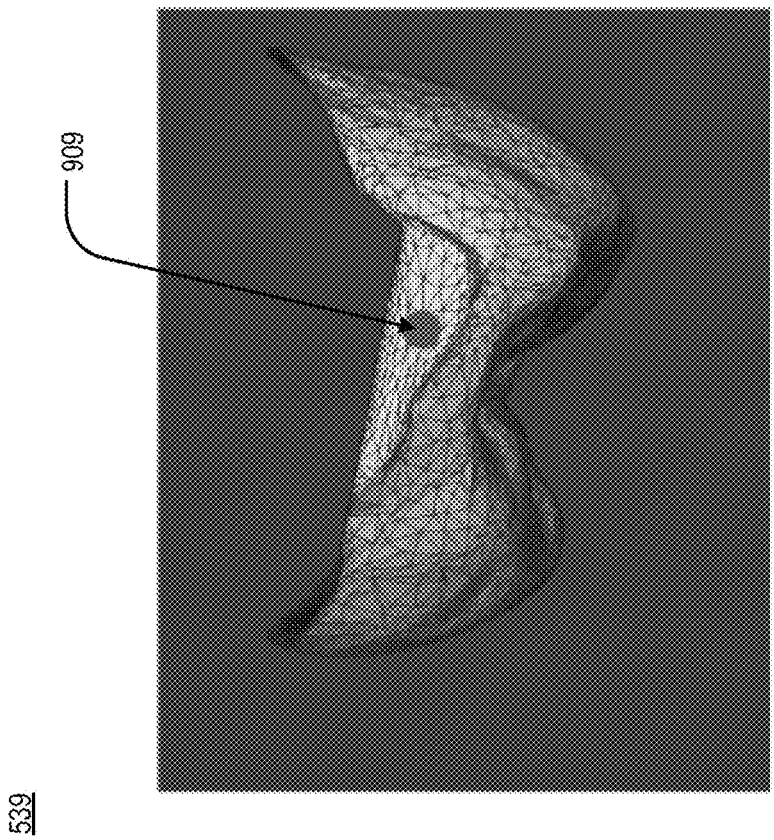
FIG. 9B is an illustration of contact point identification in a three-dimensional rendering of a tooth, according to an exemplary embodiment of the present disclosure.
Figure 9A:
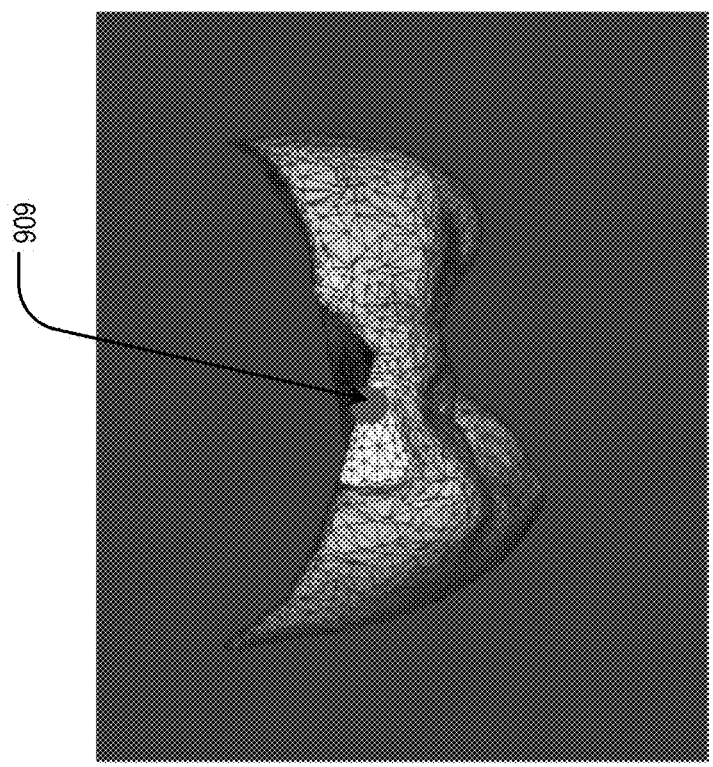
FIG. 9A is an illustration of contact point identification in a three-dimensional rendering of a tooth, according to an exemplary embodiment of the present disclosure.

Generally, the use of isolines includes creating a sectioned map of topographical features of, for instance, a tooth. Various arithmetic calculations can then be performed to identify and extract a specific feature from the map. For instance, as it relates to teeth, a main cusp of a premolar used to define a level of overlap when occlusion is modeled can be identified 533 by locating the highest nested isoline, as illustrated in FIG. 6, wherein the circular lines of the image indicate different isolines of the tooth relative to a x-dimension of the tooth and a y-dimension of the tooth. In this case, each isoline indicates an elevation relative to a plane of the image. With reference to FIG. 7B through 7E, identified dental control points, or dental features 534, in an example, are illustrated on a wire mesh (shown bare in FIG. 7A). To this end, a buccal cusp 711 can be observed in FIG. 7B, a lingual cusp ridge 712 can be observed in FIG. 7C, mesiolingual and distolingual inclines 713 and areas of contact with antagonists can be observed in FIG. 7D, and a mesiodistal fissure 714, representing an area around lowest nested isolines of the tooth, can be observed in FIG. 7E. Identified dental control points can include, with reference to FIG. 9A and FIG. 9B, contact points. In the case of a premolar, as in FIG. 9A and FIG. 9B, contact points can be indicated by circles 909 and located in positions where linear extensions of the main fissure (of FIG. 7) meet a broken isoline. In other words, the contact points may exist, in an example, at positions where the linear extensions of the main fissure no longer intersect a unique isoline.

More specifically, in order to accomplish the above, sub process 230 can be applied to each tooth of each dental arch, beginning at step 531. In step 531, isolines are calculated within the xOz plane, the xOz plane being a plane defined by the x-axis and the z-axis with an origin of 'O'. For a single tooth, these isolines may be calculated as lines of a digital dental model of the tooth that intersect with the xOz plane. Centroids can be calculated for the obtained isolines and, using a least-squares method, for instance, a vertical axis of the tooth can be constructed at step 532 of sub process 230.

At step 532, and in order to begin to identify dental features, isolines of a plane orthogonal to the vertical axis of each tooth can be calculated. In other words, each line of the digital dental model of the tooth that intersects with the plane orthogonal to the vertical axis is defined as an isoline. In one instance, a single isoline or nested isoline may be used in identifying a relevant dental feature of a tooth. In another instance, a tooth may contain more than one dental feature and, therefore, in order to identify the dental features, groups of nested isolines are required to be tracked as dental features of the tooth. To this end, in the list of calculated isolines, each series of isolines is indexed such that subsequent series of isolines may be 'embedded' within a previous series and projected to the plane. In this way, multiple nested isolines may be grouped into a larger nested group.

Figure 5A:
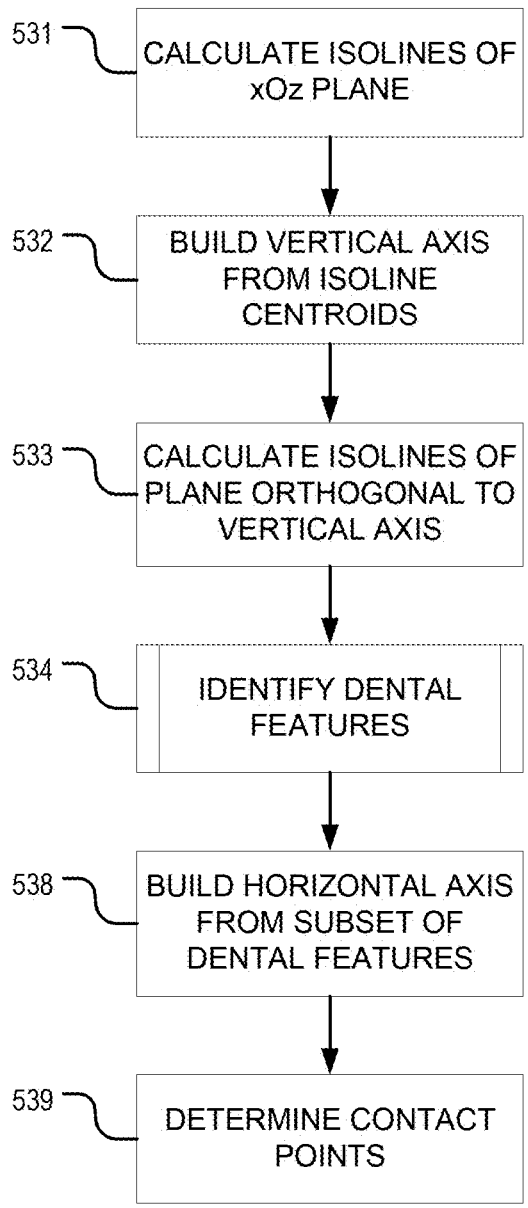
FIG. 5A is a flow diagram of a sub process of a process of an orthodontic treatment planning system, according to an exemplary embodiment of the present disclosure.
Figure 5B:
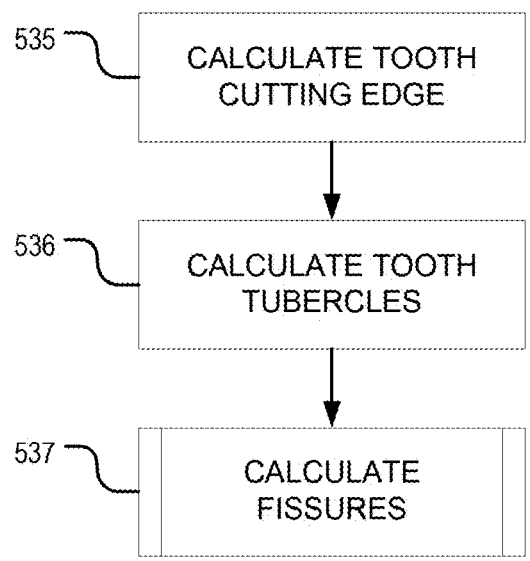
FIG. 5B is a flow diagram of a sub process of a sub process of a process of an orthodontic treatment planning system, according to an exemplary embodiment of the present disclosure.
Figure 5C:
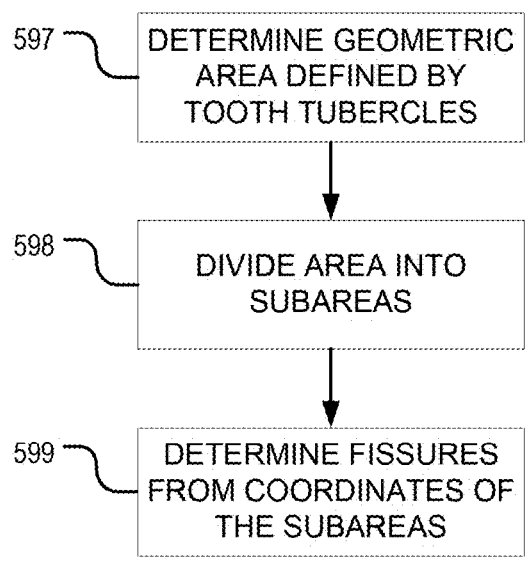
FIG. 5C is a flow diagram of a sub process of a sub process of a process of an orthodontic treatment planning system, according to an exemplary embodiment of the present disclosure.

At sub process 534 of sub process 230, and with reference now to FIG. 5B, points of maximum distance are identified for each isoline of a series. In other words, corresponding or adjacent points of an isoline are evaluated to determine which pair has a maximum distance therebetween. At step 535 of sub process 534, such corresponding or adjacent points determined to have the maximum distance therebetween are identified as defining a tooth cutting feature. As mentioned previously, the tooth cutting feature may be an incisal edge, a cusp, or the like, predicated on the tooth being analyzed. At step 536 of sub process 534, centroids of the last isoline in a series are calculated and identified as defining tooth tubercles, small elevations of variable size on a crown of a tooth representing a thickened area of enamel or an accessory cusp.

According to an embodiment, the tooth tubercles calculated in step 536 of sub process 534 are used in sub process 537 of sub process 534 in order to calculate points defining fissures of the tooth, the tooth fissures being grooves at the base of cusps or incisal edges that easily accumulate detritus. To this end, and with reference to FIG. 5C, an area generated by a polygon whose vertices are found in points of the calculated tooth tubercles is determined at step 597 of sub process 537. The area can be divided, at step 598 of sub process 537, into subareas having points with minimal coordinates along the calculated vertical axis. Such subareas, as a result, can be used at step 599 of sub process 537 to determine points that define tooth fissures.

Returning now to FIG. 5A, having identified, as dental control points, dental features including, among others, a cutting edge of a tooth, a horizontal axis can be determined. To this end, points defining the cutting edge of the tooth can be combined with a corresponding vector of the vertical axis determined at step 532 of sub process 230 in order to define the horizontal axis. In particular, the points defining the cutting edge of the tooth can be projected onto a plane orthogonal to the vertical axis of the tooth and the horizontal axis can be generated, therefrom, using a least-squares method and the projected points of the cutting edge of the tooth. It can be appreciated, however, that the least-squares method is merely exemplary of a variety of methods of performing regression analysis or similarly approximating a solution without deviating from the spirit of the invention of the present disclosure.

Accordingly, at step 539 of sub process 230, contact points as a subset of dental control points can be determined. To this end, points with largest and smallest coordinates on the Ox axis are identified. The identified points, in view of neighboring intra-dental arch and inter-dental arch teeth, form contact points that can be used in evaluating occlusion and identifying the ideal dental arch, as will be described with respect to FIG. 10 through FIG. 13.

Mentioned above, and as exemplified by the isoline approach, dental feature extraction can be performed by a variety of methods. In an example, and with reference to FIG. 8A and FIG. 8B, dental features can be extracted using a machine learning strategy such as a neural network.

According to an embodiment, the neural network-based approach can implement an artificial neural network (ANN) trained to perform (1) a segmentation approach, such as mesh segmentation, and (2) classifying, or labeling, on three-dimensional digital models of dentition or an individual tooth. In an embodiment, mesh segmentation and labeling can be combined in a single approach such as PointNet and the like. PointNet, an open-source segmentation and classification algorithm, provides a deep net architecture that consumes raw point clouds (i.e. set of points) without voxelization or rendering. In turn, PointNet learns both local and global point features, providing an efficient method for a variety of three-dimensional recognition tasks.

Considered in view of the present disclosure, an ANN can be based on a corpus of reference images including, in one case, each possible tooth type within dental arches of a patient, including an incisor, a canine, a premolar, and a molar. In another case, the ANN can be based on a generic tooth model. In either case, the ANN can then be trained to identify segments of each reference image that correspond to the above-described dental features and contact points. For instance, the segments can be identified as tubercles or cusps 807, incisal ridges 808, a lingual cusp ridge 812, a mesiodistal, or main, fissure 814, mesiolinguial and distolinguial inclines 813, and the like.

Therefore, when being implemented, in an embodiment, the ANN can perform segmentation by (1) considering all vertex points and assigning a 'class' to each vertex point or, (2) considering other mesh elements, such as faces or edges, predict classifications thereof. In either case, the result is a segmented mesh where each class, or segment, of the three-dimensional model of the tooth corresponds to a tooth feature of interest. Such result is illustrated with respect to FIG. 8A and FIG. 8B, wherein different classes, or segments, of each tooth are identified by different color regions corresponding to different dental control points of interest.

According to an embodiment, the above described sub process 230 of process 200 may be modified in the event that dental control points are difficult to identify. Specifically, it may be that the teeth of a patient are worn down over time such that naturally occurring dental control points are no longer easily identifiable, or some cases, do not exist at all. Though proxy landmarks may be used in some cases, the presence of worn down teeth often results in the need for manual intervention. When considered as a scalable process, manual intervention becomes a rate limiting step and burdensome to efficient treatment.

To this end, when there is a need to perform orthodontic treatment planning at scale (i.e. for broad implementation), it becomes important to automate processes. Automation according to process 230 as described in FIG. 5A, however, is made difficult when teeth are worn and features are not easily identifiable. When teeth are worn, as a result of malocclusion, bruxism, and the like, dental control points of the teeth, such as fissures, cusps, incisal edges, ridges, grooves, pits, and the like, may be deformed and/or missing. As such, when teeth lack the dental control points needed to generate an ideal dental arch or target dental arch that confers proper occlusion, automated systems often fail.

To this end, and as an embodiment of the present disclosure, a method is presented to generate virtual dental control points of worn teeth based on three-dimensional models of normal teeth that have been worn. The method can implement, in an instance, a machine learning approach such as a generative adversarial neural network or similar deep learning neural network. In order to accurately predict the virtual dental control points of the worn tooth, a machine learning approach must be trained. In an instance, the machine learning approach can be trained on a training dataset created from three-dimensional models of healthy teeth. In an example, the three-dimensional models of the healthy teeth may be surface mesh models. The three-dimensional models of the healthy teeth of the training dataset can be processed as in sub process 230 of process 200. Subsequently, however, certain features of the three-dimensional surface mesh model can be removed from the model in order to obtain a worn tooth. Accordingly, the training dataset consists of labeled, worn teeth that can be used to predict needed virtual dental control points from the limited anatomical features of a worn tooth.

In an example, the features removed from the model can be selected manually or automatically. An automated process may include (1) locating the feature to be worn, or 'worn out', (2) selecting a mesh area surrounding the area of the feature, and (3) performing a mesh deformation procedure. The mesh deformation procedure may be a smoothing procedure such as Laplacian mesh smoothing or Gaussian mesh smoothing, a deletion of the selected mesh area and a filling of the deleted area with a flat patch, and a deletion of the selected mesh area and a filling of the deleted area with a curved patch, the curvature of the curved patch connecting aspects of triangles located on an exposed edge of the deleted mesh area.

Figure 10:
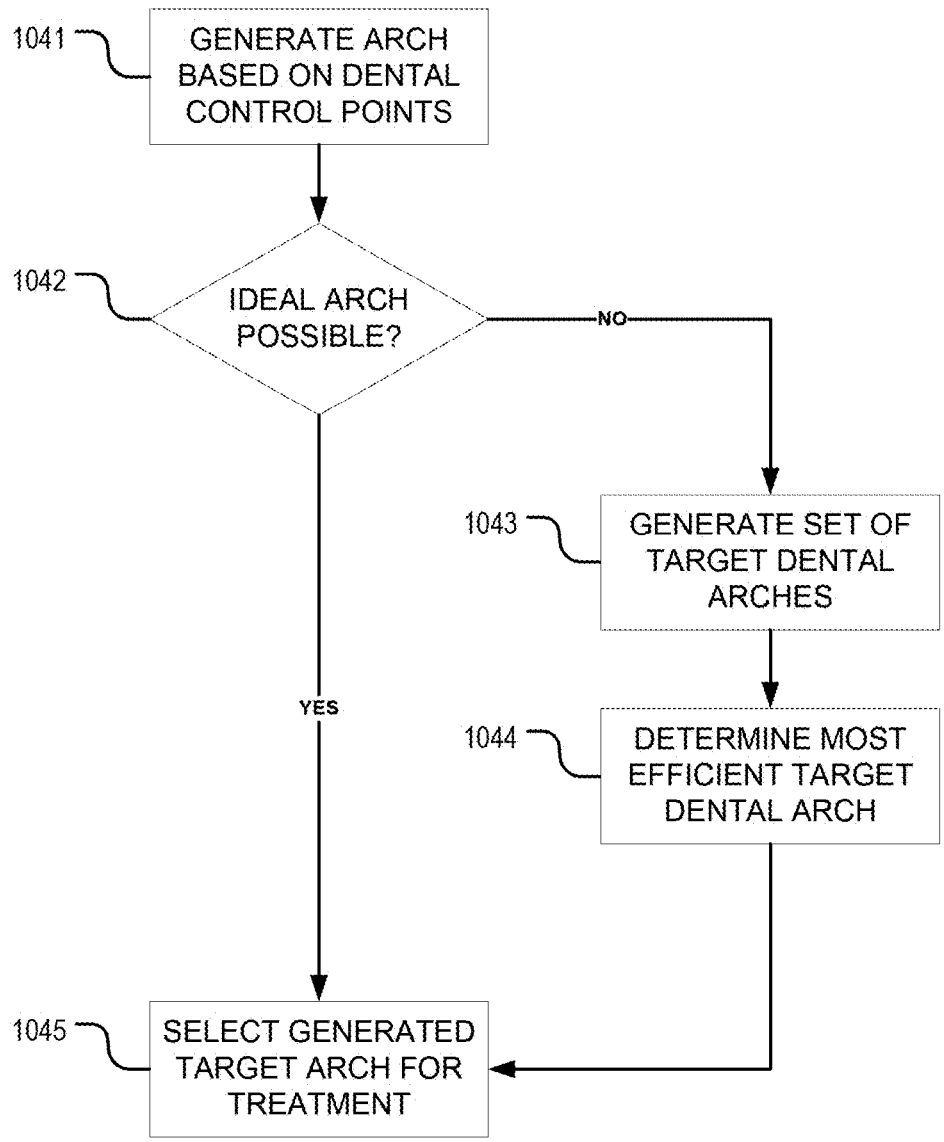
FIG. 10 is a flow diagram of a sub process of a process of an orthodontic treatment planning system, according to an exemplary embodiment of the present disclosure.
Figure 12A:
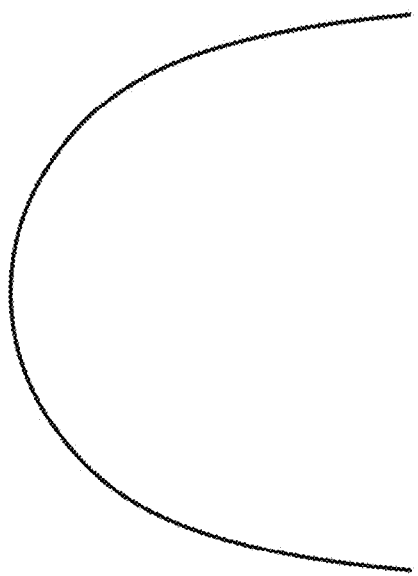
FIG. 12A is an illustration of an occlusal arch shape, according to an exemplary embodiment of the present disclosure.
Figure 12B:
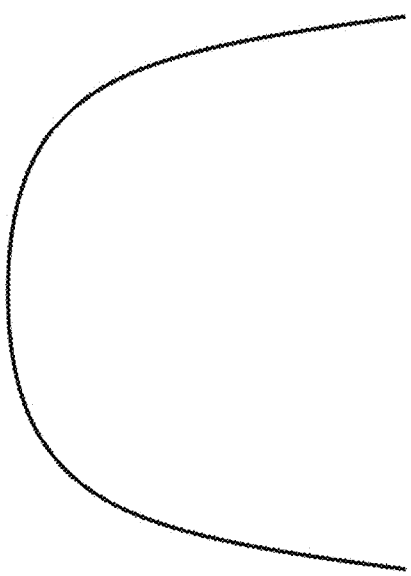
FIG. 12B is an illustration of an occlusal arch shape, according to an exemplary embodiment of the present disclosure.
Figure 12C:
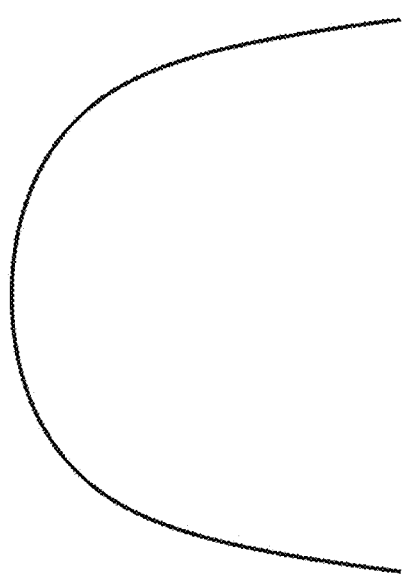
FIG. 12C is an illustration of an occlusal arch shape, according to an exemplary embodiment of the present disclosure.
Figure 12D:
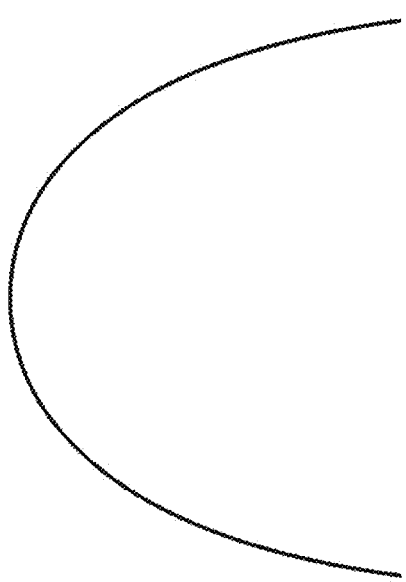
FIG. 12D is an illustration of an occlusal arch shape, according to an exemplary embodiment of the present disclosure.

With reference now to FIG. 10, after identification of dental control points, including dental features and contact points, an ideal dental arch can be determined. The ideal dental arch can represent, if possible, the ideal final position of each tooth and indicate what teeth movements from the initial dental arch may be necessary. Described in FIG. 10, and with reference again to FIG. 2, the determination of the ideal dental arch is performed by sub process 240 of process 200.

Briefly, generation of an ideal dental arch, in view of alignment, arch shape, and occlusion employs an iterative process that considers local bases, reference intervals, control points, and the like. This process allows for, in an ideal case, generation of a dental arch that avoids collisions and clashes during teeth movement from an initial dental arch position 1146, as illustrated in FIG. 11, to a final dental arch position. Once generated, the ideal dental arch can be used as a target position 1147 for teeth of the dental arch of the patient with phases, and stages thereof, for achieving this target position 1147 calculated therebetween.

Informing the generation of the ideal dental arch is occlusion. As a general guideline, occlusion of ideal dental arches is understood to mean the position and arrangement of dentition of a patient that conforms to orthodontic rules and principles of health and beauty. More specifically, occlusion of ideal dental arches is based on known orthodontic criteria of good occlusion, defined in each anatomical plane of the teeth. These criteria can include, in a sagittal plane: (1) contact between the mesiobuccal cusp of the first molar of the maxillary dental arch and the intersection of the longitudinal fissure and transverse fissure of the first molar of the mandibular dental arch; (2) contact of an incisor of the maxillary dental arch with the rear ridge of a corresponding incisor and the front ridge of a premolar of the mandibular dental arch; (3) contact between the maxillary incisors and the mandibular incisors; (4) overlap of the mandibular incisors by the maxillary incisors; and (5) a 120° angle between incisors. These criteria can further include, in a coronal plane: (1) overlap of the mandibular incisors by the maxillary incisors up to ⅓ of a height of a crown of a respective mandibular incisor; and (2) contact between premolars and molars of the maxillary dental arch and the mandibular dental arch. Moreover, these criteria can include, in a transverse plane: (1) overlap of the mandibular molars by the maxillary molars equal to a size of a cusp of the maxillary molar.

In addition to the above, a shape of an ideal dental arch and, accordingly, occlusion, can be informed by an occlusal arch length, the occlusal arch length being measured as a sum of mesiodistal sections of each tooth in a respective arch. In an embodiment, the shape of the ideal dental arch can be chosen from empirical analytic curves or determined in line with orthodontic rules and dental arch tests received as patient-related information at step 220 of process 200. For instance, understanding the occlusal arch length or segments thereof permits assumptions with regard to occlusal arch shapes and distances between dental control points based on Pont's index, Tonn's index, the Bolton relationship, and Kornhaus's index, among others. To this end, and as an example, these relationships can be defined as Σ(mesiodistal sections of 4 incisors)*1.25=(distance between first premolars) and/or $$\sum (\text{mesiodistal sections of 4 incisors}) * \frac{100}{64} =$$

(distance between first molars).

As described, mesiodistal dimensions of each tooth within each dental arch can be evaluated to determine feasibility of an arch shape. Such occlusal arch shapes are represented in FIG. 12A through FIG. 12D, respectively.

To begin a more detailed description of sub process 240 of process 200, the digital dental model and dental control points, including dental features and contact points calculated from previous sub processes, can be used at step 1041 to generate an ideal upper dental arch and an ideal lower dental arch. As introduced above, the optimization of the ideal dental arch shape is performed on the basis of, at least, input data and input restrictions on interdental spaces (i.e. fitting of a curve). In an example, the input data may include dental control points including local axes of each tooth, a defined shape of the arch, interdental distances, and the like, the input data serving as reference points and geometric parameters for generation of a new shape. In addition, each ideal dental arch shape can be selected, as mentioned, from a list of empirical analytic curves or determined in accordance with rules, orthodontic recommendations, and tests of the dental arch. In complex cases, when, for instance, an optimization is unable to determine solutions using set parameters, the set parameters and, moreover, methods of optimization, can be changed automatically or manually by an operator.

As indicated above, it may be that, in view of dental collisions and the like, an ideal dental arch is impossible to achieve and, accordingly, it is not a suitable target dental arch. Therefore, having generated an ideal dental arch based on dental features and contact points at step 1041 of sub process 240, the generated ideal dental arch is evaluated to determine its feasibility. For instance, it can be determined whether the ideal position can be achieved, as described in the example in FIG. 11, without causing dental collisions of neighboring teeth.

Accordingly, at step 1042 of sub process 240, possible dental collisions of the ideal dental arch can be assessed. Fast detectors of possible collisions and slower methods for locating collisions of three-dimensional models of teeth can be used to detect the number of model intersections. If a quantity of detected model intersections is less than a pre-determined threshold value, the generated ideal dental arch is deemed possible and the sub process 240 proceeds to step 1045, wherein the generated ideal dental arch is selected as a target dental arch for subsequent treatment-related processing. If, however, the quantity of detected model intersections is greater than a pre-determined threshold value, the generated ideal dental arch is determined to be impossible and sub process 240 proceeds to step 1043.

At step 1043 of sub process 240, a library of possible, 'near-ideal' dental arches, or possible target dental arches, can be generated, each possible target dental arch being a dental arch that eliminates the dental collisions found in the generated ideal dental arch, as well as those subsequently generated during processing of each possible target dental arch. To this end, the generation of each possible target dental arch is iterative, as dental collisions between neighboring teeth are detected and then eliminated. Described in more detail with reference to subsequent figures, the search for dental collisions of neighboring teeth is illustrated in FIG. 15. The result of step 1043 is a set of possible target dental arches that minimize dental collisions while approximating the generated ideal dental arch.

At step 1044 of sub process 240, each of the set of generated possible target dental arches are evaluated to determine the most effective possible target dental arch. This analysis can be performed by minimizing a cost function or the like or can be based on a set of custom functions or nested functions based on the above-noted criteria of good occlusion. In the case of one or more nested functions, which can be configured to generate a metric or a measure of quality of 'bite' or occlusion, each nested function can be evaluated at the level of a single tooth, a single dental arch, or the upper dental arch and lower dental arch combined. Examples of features that can be evaluated by the one or more nested functions include: (1) a distance between dental control points (e.g., dental features, contact points, and the like): (2) angulation of each tooth; and (3) occlusal arch shape.

In an embodiment, and as introduced above, the metric may be evaluated for quality of a 'bite' at the level of a single tooth. In this case, the nested function can perform a series of operations. First, in an example, a distance between a current position of a tooth from a target position can be computed, taking into account current rotation and translation parameters of the tooth in a global coordinate system resulting in transformation matrices for the local coordinate system of the tooth. Second, weight indices for each of the distance position parameters can be determined, the weight indices being set for each of rotation about each axis and axial translation in the local coordinate system of the tooth. Lastly, the metric, or statistical metric, can be computed therefrom. The statistical metric may be an average value, in an example.

In an embodiment, and as introduced above, the metric may be evaluated for quality of a 'bite' at the level of a single dental arch. In this case, the nested function can perform a series of operations. First, in an example, (a) a distance between a current position of dental control points of each tooth and an ideal position of respective dental control points of each tooth and (b) a distance between a current position of dental control points of each tooth and a current position of corresponding dental control points of neighboring teeth can be calculated. Second, weight indices for each of the distance position parameters can be determined, the weight indices being set for each of (a) the distance between the current position of dental control points of each tooth and the ideal position of respective dental control points of each tooth and (b) the distance between the dental control points of each tooth and the current position of corresponding dental control points of the neighboring teeth. Lastly, the metric, or statistical metric, can be computed therefrom. The statistical metric may be an average value, in an example.

In an embodiment, and as introduced above, the metric may be evaluated for a quality of a 'bite' at the level of the mouth, including both dental arches. In this case, the nested function can perform a series of operations. First, a distance describing a current positional relationship between anatomical features of teeth of a mouth can be calculated in view of an ideal positional relationship between the anatomical features, or dental features, of the teeth of the mouth, the distance being defined, in part, by existing orthodontic knowledge. In an example, the distance can be a distance between the mesiolingual cusp of the first maxillary molar and the mesiodistal fissure of the antagonistic first mandibular molar, wherein the target relationship between them is a distance of zero (reflecting contact therebetween). The distance may also be a distance between a mesiolingual incline and a distolingual incline of the maxillary canine and a distobuccal incline and a mesiobuccal incline of corresponding antagonistic teeth, the corresponding antagonistic teeth being a canine and a first premolar and the target relationship between them being a distance of zero (reflecting contact therebetween). In another instance, the distance may be an amount of overlap between maxillary incisors and mandibular incisors, wherein the target relationship between them is an overlap distance of ⅓ of the height of the crown of the maxillary incisors. In another instance, the distance may be an inclination angle between the front incisors, wherein the target relationship between them is an inclination angle of 139. Second, weight indices for each of the distance position parameters can be determined. Lastly, the metric, or statistical metric, can be computed therefrom. The statistical metric may be an average value, in an example.

Figure 14:
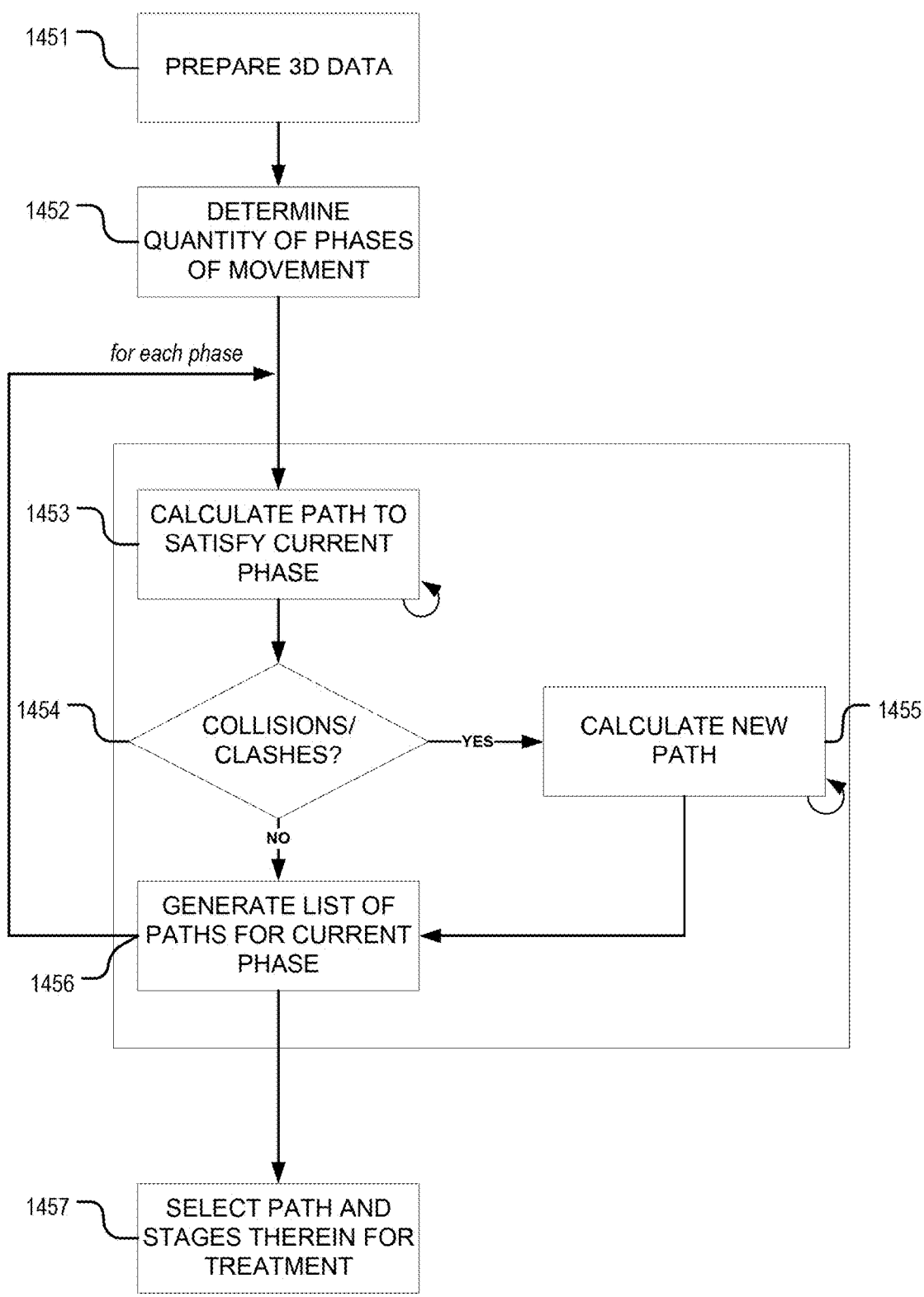
FIG. 14 is a flow diagram of a sub process of a process of an orthodontic treatment planning system, according to an exemplary embodiment of the present disclosure.
Figure 15:
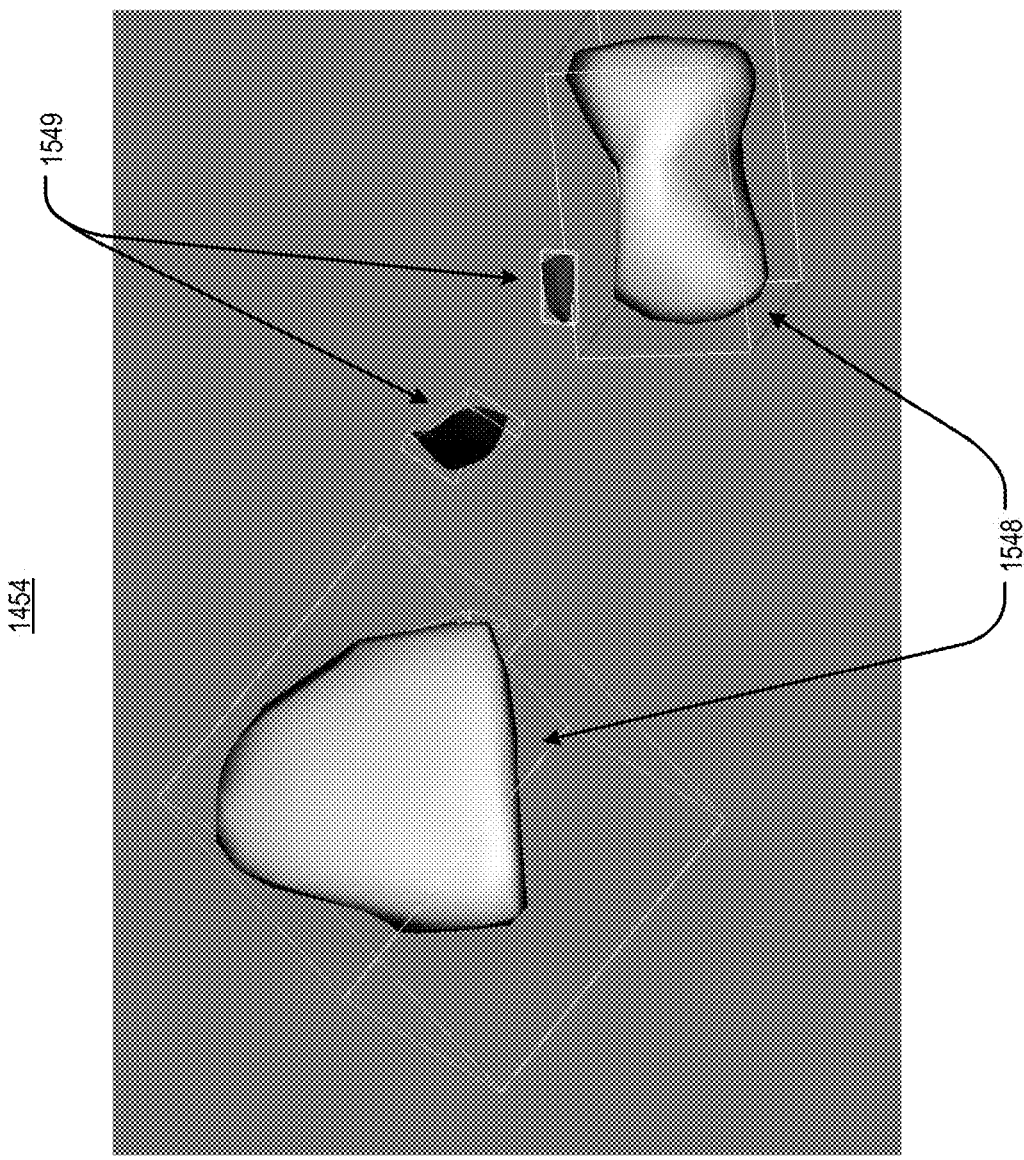
FIG. 15 is an illustration of a three-dimensional rendering of dental collisions, according to an exemplary embodiment of the present disclosure.

The above-described statistical metrics can be similarly generated, with reference to FIG. 14, for each stage of teeth movement and/or for each phase of teeth movement. At each phase of teeth movement, for instance, the ideal positions referenced above can be modified in view of the target intermediary teeth positions. In such case, target intermediary teeth positions can become a de facto ideal position. Therefore, it can be appreciated that the evaluation of quality of the 'bite' can be similarly used to inform selection of an appropriate tooth movement within each phase.

In view of any of the nested functions proposed above, step 1044 determines which one of the set of generated possible target dental arches minimizes the nested function or reduces the output metric of the nested function below, or increases the output metric of the nested function above, a pre-determined threshold value. Accordingly, at step 1045 of sub process 240, the most efficient possible target dental arch can be selected as the target dental arch for subsequent treatment-related processing.

Figure 13:
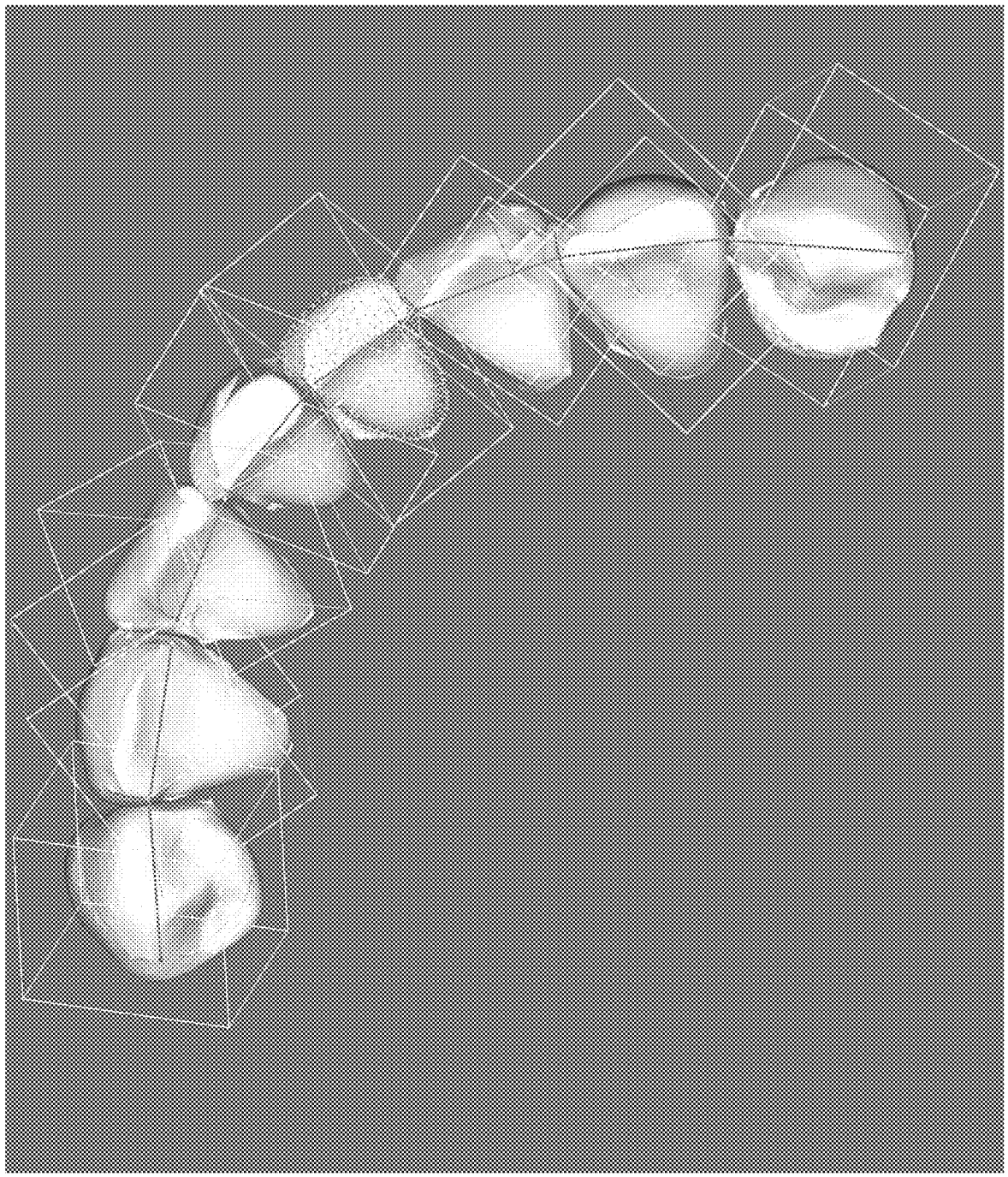
FIG. 13 is an illustration of a three-dimensional rendering of a near-ideal dental arch, according to an exemplary embodiment of the present disclosure.

According to an embodiment, FIG. 13 provides an illustration of a result of the above-described search for a target dental arch, dental control points (e.g., dental features and contact points), and teeth movements in achieving the target dental arch.

In an embodiment, each possible dental arch, including the selected target dental arch, can be calculated automatically by the OTPS or, in more complicated cases, can be calculated manually under the control of an operator.

In an embodiment, teeth movement stages, described with respect to FIG. 14, can be based on the selected target dental arch or target intermediary teeth positions thereof. Additionally, the selected target dental arch shape can be used for forecasting treatment.

It can be appreciated that sub process 240 of process 200 provides a set of advantages over other approaches. As a result, in determining the target dental arch, the need for treatment-dependent data is eliminated. For instance, the OTPS utilizes two-dimensional data and/or three-dimensional models of teeth generated prior to treatment, allowing for an orthodontic treatment plan to be based on a baseline condition of the patient with dental control points identified therefrom.

Returning to the figures, having identified the target dental arch or target dental arches for a patient, teeth movements must be determined in order to move from an initial position to the target dental arch. With reference now to FIG. 14, sub process 250 of process 200 will be described. Generally, sub process 250 includes receiving the selected target dental arch from sub process 240 and determining the phases of movement from the baseline position to the target position. In an embodiment, each phase of teeth movement can be defined as an intermediate position of a dental arch defining target intermediary teeth positions in view of orthodontic restrictions that may be general or patient-specific. Such orthodontic restrictions applied to the phase may include "three neighboring teeth cannot be simultaneously moved" while an orthodontic restriction applied to movement of each tooth with the dental arch can included "an aligner cannot move a tooth more than 250 microns". Information about the orthodontic restrictions, the intermediate positions of each tooth, and treatment progress can be stored within a database and used for monitoring a condition of a patient, forecasting a condition of the patient, and/or correcting the orthodontic treatment plan of the patient in real-time. It can be appreciated that such process can be performed for both of the target maxillary dental arch and the target mandibular dental arch.

More specifically, sub process 250 of process 200 begins at step 1451. At step 1451, three-dimensional data, based on the extracted dental control points and the received one or more medical images, can be prepared. This can include modification of data associated with each tooth such that local bases (e.g., axes) are transformed to be within a single, global coordinate system. The single coordinate system creates a feedback system wherein any deviations in teeth positions responsive to anticipated dental collisions can be determined in view of a specified movement goal (e.g. target position of the target dental arch). The prepared three-dimensional data reflects a baseline position of a corresponding target dental arch and may include, in an example, polygonal teeth models similar to those of the target dental arch illustrated in FIG. 13.

At step 1452 of sub process 250, a quantity of required teeth movement phases can be determined based on a difference between the input baseline positions and selected target dental arch positions and in view of orthodontic-based movement restrictions such as those described above. As introduced previously, each phase of teeth movement can define an intermediary position of the teeth.

Having determined the quantity of teeth movement phases required to reach the target dental arch and, therefore, intermediary teeth positions therebetween, one or more paths can be calculated at each phase and for each tooth of each dental arch of the maxillary dental arch and the mandibular dental arch, an optimal path being selected therefrom. Each of the one or more paths may include one or more teeth movement stages, each teeth movement stage reflecting a single trajectory, or vector, in gradually moving each tooth toward and intermediate position.

To this end, beginning at step 1453 of sub process 250, one or more possible paths may be calculated for a first tooth of a dental arch during a first teeth movement phase. The one or more paths may be calculated such that the first tooth can be moved to a first intermediate position from the baseline position, during the first teeth movement phase, the one or more paths describing all possible paths for the first tooth to achieve the first intermediate position. Similar calculations can be performed for the remaining teeth of the dental arches for the first teeth movement phase. The one or more paths can be calculated in view of orthodontic rules of angular movement and linear movement, the calculations aided by Euler angles and quaternions in an example. Restrictions on speed and trajectory can be accounted for as derivations from the orthodontic rules for ranges of angles and movements and the number of moving teeth, depending on the complexity of the treatment course. Further, control of angular motion in local coordinates is performed with the help of Euler angles and quaternions with breakdown of transformation into orthodontic relocations and rotations.

A result of the calculations is a tree of possible paths of teeth for the first teeth movement phase. Each calculated path for each tooth creates a new branch and/or leaf of the tree of possible paths. In an embodiment, the algorithm grows new branches to the tree when necessary and cul-de-sac branches may be trimmed to save computational resources. To this end, the tree of possible paths includes nodes between branches and leaves, each node being a data structure that consists of several elements, including: (1) information describing a possible path, (2) a path trajectory or trajectories for each tooth, (3) optimization criteria (e.g., a node can be put to idle state to save computing power if deemed non-optimal, while an idle node may be activated if the current main branch is considered to lead to a dead-end). Further, each node of the tree of possible paths includes all information required to: (1) restore a path and (2) create a new path.

At process 1454 of sub process 250, the calculated paths can be evaluated to determine if dental collisions (i.e. collisions/clashes) will occur and to ensure that orthodontic prescriptions and restrictions are carried out. This includes, in an example, rough evaluation of overlaps of the polygonal teeth models in addition to more refined evaluation of the precise three-dimensional shape of each tooth. Such evaluation is illustrated in FIG. 15. As in FIG. 15, a bounding box and/or other rapid evaluation of possible overlaps are used only for initial testing of clashes. Such initial testing can indicate regions of teeth that are colliding 1549 and regions of teeth that are free of collisions 1548. Refined evaluations of a precise three-dimensional shape of each tooth include the use of penalty functions and optimization criteria. If dental collisions are found at step 1454 of sub process 250, trajectories of a new path may be calculated at step 1455 of sub process 250 and added to the tree of possible paths as branches and/or leaves, as appropriate.

In an embodiment, upon identifying dental collisions at step 1454 of sub process 250, it may be initially determined as impossible to overcome the dental collisions. As a result, several different approaches may be executed independently or in combination to eliminate such dental collisions. These approaches can include algorithm search strategies such as (1) depth-first search and adjustment of process history at a previous trajectory of a path and (2) transition to an earlier state of the teeth movement system without deleting yet untested branches. Further, these approaches can include a clinical strategy such as (3) expanding the dental arch. Other clinical strategies include inter-proximal enamel reduction (IPR) and the like. To this end, a thickness of an oriented bounding box of an intersection of two collided teeth, as in FIG. 15, can be measured. If the thickness is within an acceptable IPR threshold, the acceptable IPR threshold being unique for each tooth and stored within a database, the collision of the two teeth can be listed as acceptable. However, if the thickness is outside of the acceptable IPR threshold, an IPR can be performed. Each method described above overcomes the dental collisions and engenders new branches and/or leaves of the tree of possible paths.

After generating the tree of possible paths and accounting for possible dental collisions, a list of acceptable paths can be generated, as a complete tree of possible paths, at step 1456 of sub process 250. Each acceptable path of the list of acceptable paths can be optimized according to orthodontic rules and with the goal of minimizing the quantity of teeth movement stages and number of individual teeth movements thereof.

Step 1453 through Step 1456, described above, may be repeated for each teeth movement phase determined at step 1452.

At step 1457 of sub process 250, the list of acceptable paths, or the complete tree of possible paths, can be evaluated and a treatment path can be selected. In an embodiment, a search for an optimal path in the tree of possible paths can be performed. Such search may include an estimation of efficiency and efficacy. In an instance, a path that allows a target dental arch position to be reached may be selected and extraneous paths may be removed from the tree of possible paths. In another instance, it may be found that no path allows for the target dental arch position to be reached due to dental collisions or orthodontic constraints. In this instance, the tree of possible paths can be searched and a path that minimizes a cost function may be selected. The cost function can be, in an example, a measure of quality of occlusion or a quantity of teeth movement stages. The quality of occlusion can be an evaluation of quality of 'bite', as previously described with reference to step 1044 of sub process 240.

In an embodiment, with respect to complicated cases, Step 1453 through Step 1457 of sub process 250 can be performed for each teeth treatment phase and the result thereof can be used to generate possible paths for a subsequent teeth treatment phase.

Figure 16B:
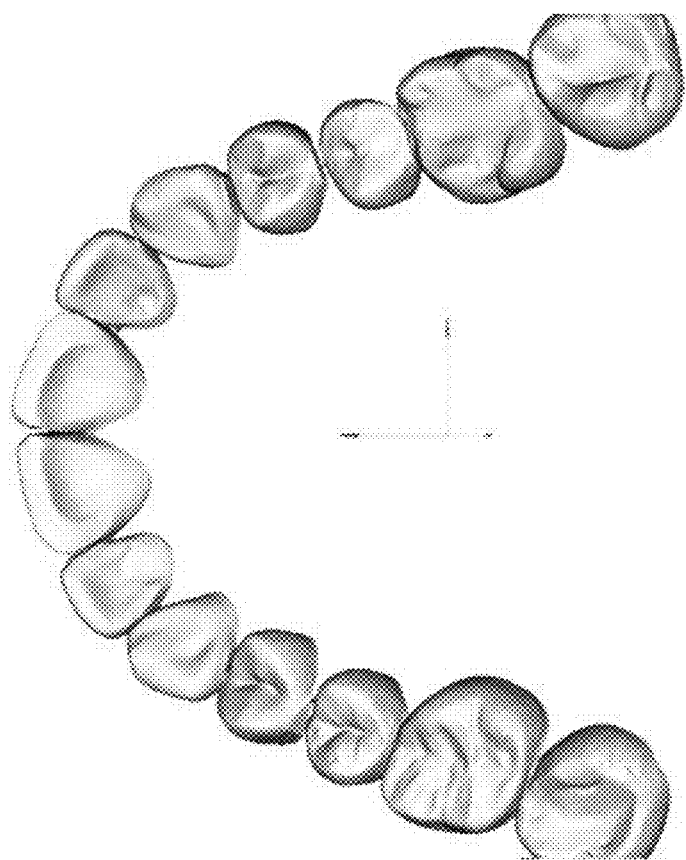
FIG. 16B is an illustration of an upper dental arch following movement towards an ideal dental arch, according to an exemplary embodiment of the present disclosure.
Figure 16A:
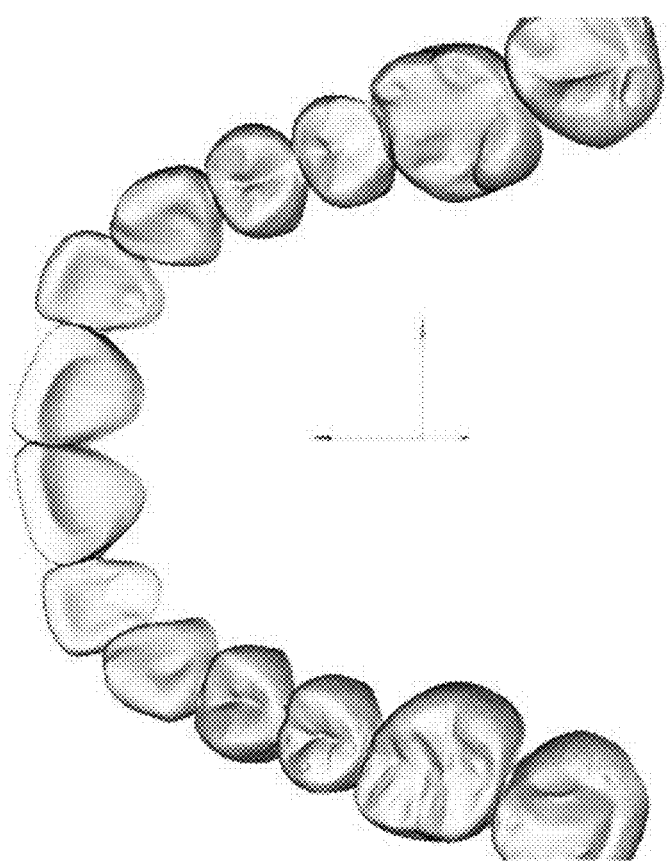
FIG. 16A is an illustration of an upper dental arch prior to movement, according to an exemplary embodiment of the present disclosure.

According to an embodiment, FIG. 16A and FIG. 16B are illustrations of three-dimensional models of a maxillary dental arch before and after orthodontic treatment, respectively.

According to an embodiment, it can be appreciated that the above-described process for automated treatment planning can be divided into three major processes: (1) identifying dental control features of each tooth, (2) defining a target position for each tooth, and (3) finding an effective and efficient path from an initial position to the target position for each tooth. These processes will be generally-described below as may be applied to the OTPS in an embodiment of the present disclosure.

In the first process, a target tooth position can be defined. Using three-dimensional mesh surface models (such as in FIGS. 7A through 7E) or volumetric models, anatomical features of teeth can be identified and target teeth positions can be determined therefrom. In an example, the anatomical features of the teeth can be dental control points as derived in sub process 230 of process 200. Next, in an example, a target tooth position can be calculated by (1) creating a metric defining a positional difference between anatomical features or dental control points and (2) minimizing the metric using a heuristic approach such as, among others, A-star, Iterative Deepening A-star, and other iterative methods. Alternatively, in an example, a target tooth position can be determined by (1) calculating an optimal position between anatomical features or dental control points based on known anatomical constraints such as, among others, Bolton analysis metric, curve of Spee shape, and ideal arch form, and (2) training a mathematical model, according to three-dimensional mesh surface models or volumetric models of the tooth, to predict the target position of the tooth based on reference data retrieved from a training dataset. In an example, the mathematical model for predicting the target position may be a statistical model, an artificial neural network, or the like based on previous patients with relevant, labeled anatomical data from before and after orthodontic treatment. An output of the mathematical model may be obtained in various formats. For instance, the mathematical model may be trained to predict a transformation matrix for each tooth, the mathematical model being trained to provide segmentation (e.g., U-nets for two-dimensional and three-dimensional segmentation or PointNet for surface mesh segmentation). The transformation matrix, or teeth movement matrix, can be a movement vector, a quaternion or a transformation class selected from a preset list of transformation classes. The preset list of transformation classes can be one of 'distal-mesial', 'buccal-lingual', 'tip', 'torque', 'rotation', 'angulation', and the like. In another instance, the mathematical model may be trained to predict a shape of a correctly positioned tooth, a transformation matrix being able to be derived therefrom. Such a mathematical model may be a deep neural network such as a generative adversarial neural network and the like. Subsequent to the prediction of the shape of the correctly positioned tooth, registration algorithms, such as iterative closest point, random sample consensus, and the like, can be used to obtain the transformation matrix for each tooth.

Subsequently, in the second process, the most effective and efficient path can then be identified. To this end, methods aimed at determining the "shortest path" may be used to determine the most effective and efficient path of each tooth and at each phase. In an instance, a method such as A*, Iterative Deepening A*, Johnson's algorithm, and the like may be used to determine a path from an initial position to a target position or target intermediary position of the tooth for each phase. At each stage of the determined path, a three-dimensional model intersection check can be performed to prevent dental collisions and, if found, iterations can be performed to determine new paths. Then, a path for a subsequent phase can be predicted. In an example, a trained mathematical model can be used to perform the above-described calculations. For instance, the trained mathematical model can be a machine learning model such as perceptron with proximal policy optimization, recurrent neural networks, Markov models, support vector machines, Bayesian models, and the like. As before, if the predicted path for the subsequent phase results in a dental collision, the trained mathematical model provides an iterative prediction in order to avoid the dental collision. In an example, the mathematical model is trained to incentivize moving closer to the target intermediary tooth position or target position of the tooth.

Figure 17:
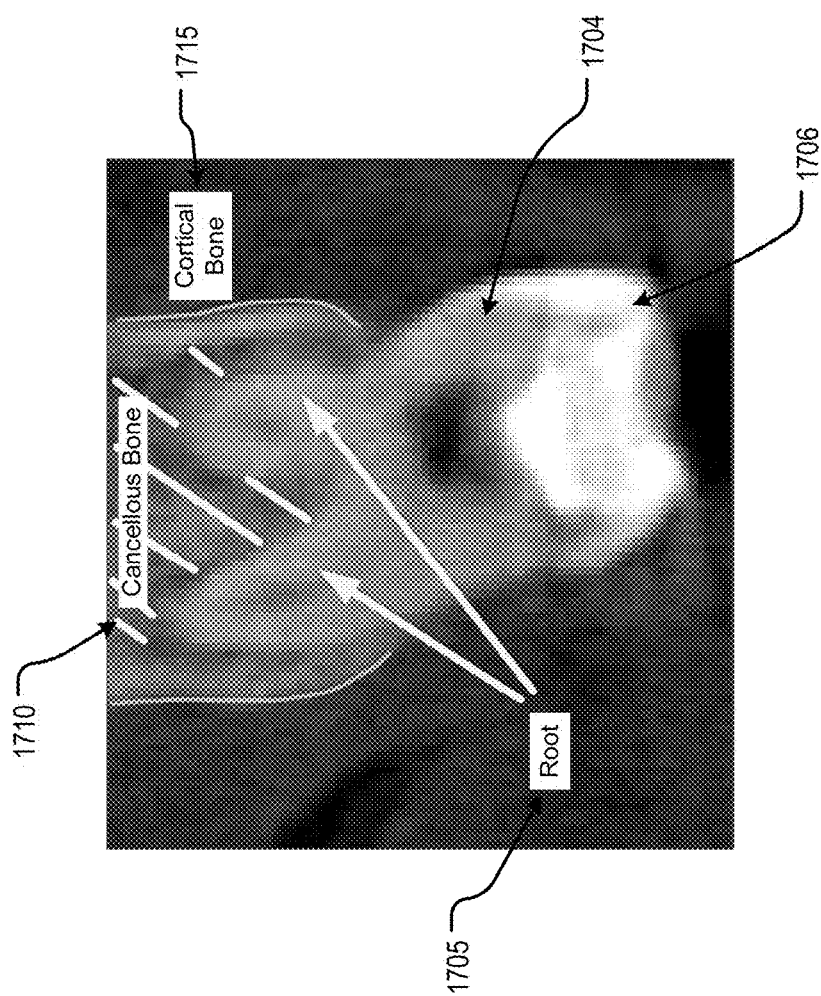
FIG. 17 is an illustration of a dental image of a tooth, according to an exemplary embodiment of the present disclosure.

Returning now to the figures, and in consideration of alternative embodiments of the invention of the present disclosure, FIG. 17 is an illustration of a dental image of a tooth. According to an embodiment of the present disclosure, the tree of possible paths and selected path that forms the backbone of the orthodontic treatment plan can be generated in view of a crown of a tooth. Additionally, the tree of possible paths can be generated in view of a complete architecture of the tooth, including both the crown of the tooth and an at least one root of the tooth. As can be appreciated, consideration only of the crown of the tooth in determining an orthodontic treatment plan risks damage to the at least one root, periodontal ligament, and periodontal bone upon movement from an initial position to a target position. In order to incorporate information related to the soft tissue and hard tissue environment of the tooth during orthodontic treatment planning, an approach for identifying tissue types, generating a three-dimensional model therefrom, and determining periodontal tissue characteristics thereof, is required. To this end, it becomes necessary to develop a strategy for discerning soft tissues from hard tissues and tooth roots from surrounding bone of varying densities. FIG. 17 is an illustration of a dental image of a tooth, according to an embodiment of the present disclosure. In an embodiment, a dental image of a tooth may be but is not limited to an image acquired via intraoral optical imaging, impressions, dental models, ultrasound, or radiography, as described above. In an example, a plurality of images, or slices, may be acquired via radiography and reconstructed to render a three-dimensional model. With reference again to FIG. 17, a tooth 1704 comprises a crown 1706 and one or more roots 1705. The one or more roots 1705 are resident within an alveolar process, a thickened ridge of bone containing dental alveoli, or tooth sockets. The alveolar process is comprised of cortical bone 1715, a compact, relatively dense bone, and cancellous bone 1710, a spongy, relatively porous bone. Together, cortical bone 1715 and cancellous bone 1710 provide a strong foundation from which the one or more roots 1705 of the tooth 1704 are anchored. As related to the present disclosure, cortical bone 1715 and cancellous bone 1710, as periodontal tissues, contribute to the determination of possible movements of a tooth.

In planning a tooth movement such that the tooth and periodontal environment are considered concurrently, a variety of structures, including those described above, must be identified. Moreover, once these features have been identified for a single two-dimensional dental image, the same can be performed for additional two-dimensional dental images, or slices, until a three-dimensional model can be rendered, therefrom. In addition to providing for aesthetic evaluation, a three-dimensional model synthesizes information regarding periodontal tissue density and thickness, thereby bounding possible tooth movements and providing a prescribing medical professional a tool from which to determine possible ranges of tooth movement.

A method of such identification of the root 1705 of the tooth 1704, for instance, as separate from the crown 1706 of the tooth 1704, has been previously described by the inventors of the present disclosure in U.S. patent application Ser. No. 16/017,687, incorporated herein by reference.

In addition to the teachings of the U.S. patent application Ser. No. 16/017,687, a machine learning-based approach may be used to identify each of at least one root 1705 of a tooth 1704 and a crown 1706 of the tooth. For instance, the machine learning-based approach may be a combination of artificial neural networks for detection and segmentation of one or more medical images. To this end, the combination of artificial neural networks may include an artificial neural network, such as RetinaNET and the like, to detect the presence of teeth of one or more medical images. The one or more medical images may be two-dimensional image slices or three-dimensional image volumes or surface meshes. The artificial neural network may be trained to isolate each tooth within a bounding box. Subsequently, a three-dimensional fully convolutional neural network, such as U-net and the like, can be trained to perform segmentation on the bounded sub-volumes, the segmentation identifying tissues of interest within the tooth, such as the at least one root 1705 and the crown 1706.

During implementation, the combined trained neural networks can process one or more medical images in a similar manner. For instance, the combined artificial neural networks can receive, as an input, a medical images volume of dental arches, or dentition, of a patient. Each tooth of the dental arches can be isolated from the medical images volume by the artificial neural network. The three-dimensional fully convolutional neural network can then be applied to the isolated teeth to generate a segmentation thereof. Finally, the segmented volumes can be converted to polygonal mesh surface models that can be integrated into an orthodontic treatment planning system, such as the OTPS of the present disclosure, wherein the segmented volumes demarcate which areas of the tooth are root and which areas of the tooth are crown, allowing movements to be planned in view of biological restrictions of the respective tissue types.

It can be appreciated, however, that one or more medical images of a patient may not be available and, therefore, a deep neural network approach such as a generative adversarial neural network or similar may be used to generate surface models of the at least one of a tooth and a crown of the tooth. For instance, the generated surface model may be of a root of a tooth.

Figure 18:
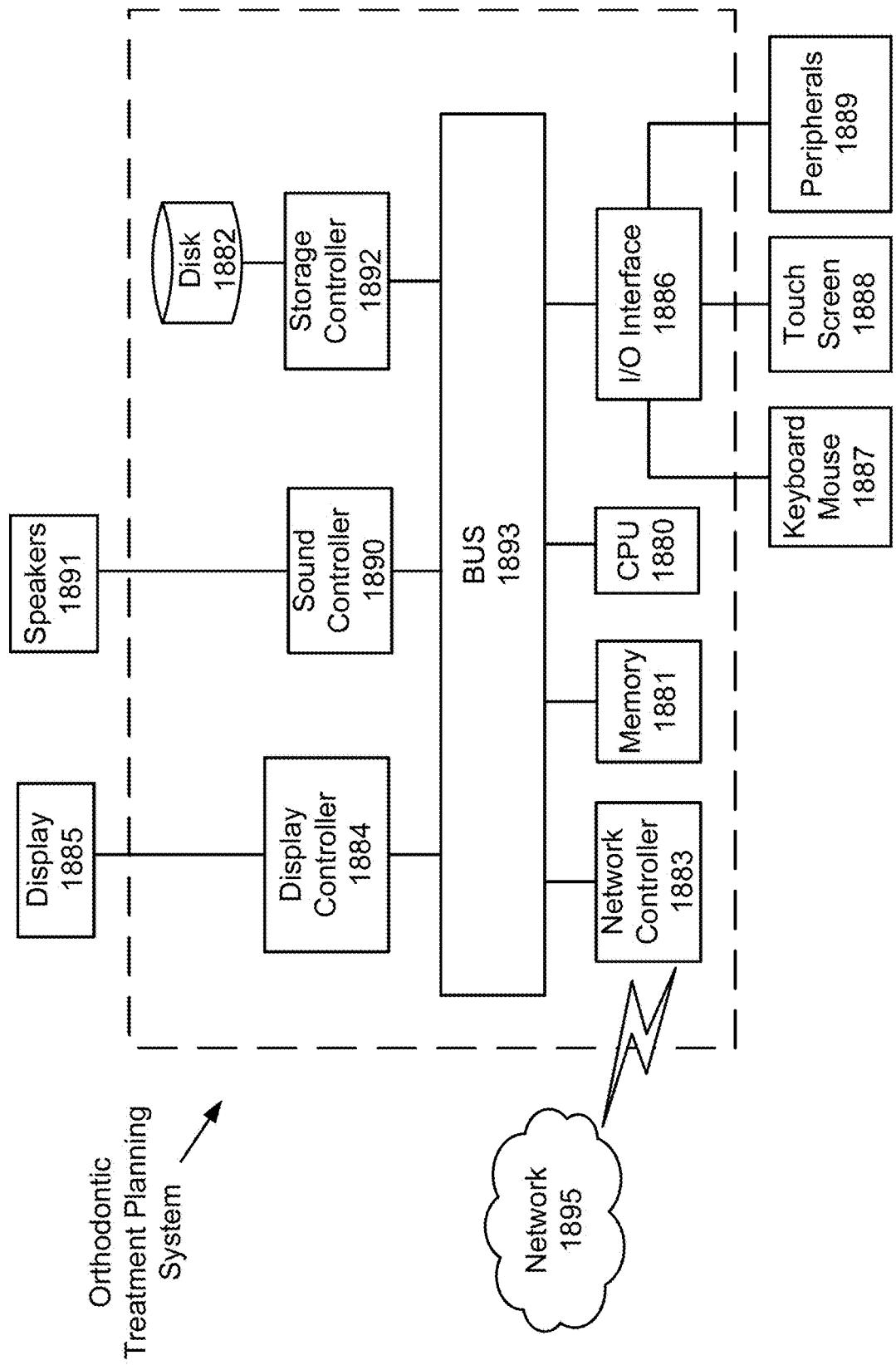
FIG. 18 is a schematic of exemplary hardware for implementing an orthodontic treatment planning system, according to an exemplary embodiment of the present disclosure.

Next, a hardware description of the orthodontic treatment planning system (OTPS), according to exemplary embodiments, is described with reference to FIG. 18. In FIG. 18, the OTPS includes a CPU 1880 which performs the processes described above/below. In another embodiment, the processing device may be a GPU, GPGPU, or TPU. The process data and instructions may be stored in memory 1881. These processes and instructions may also be stored on a storage medium disk 1882 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the OTPS communicates, such as a server or computer.

Further, the claimed advancements may be provided as a utility application, background daemon, or component of an operating system, or combination thereof, executing in conjunction with CPU 1880 and an operating system such as Microsoft Windows 7, Windows 8, Windows 10, UNIX, Solaris, LINUX, Apple MAC-OS and other systems known to those skilled in the art.

The hardware elements in order to achieve the OTPS may be realized by various circuitry elements, known to those skilled in the art. For example, CPU 1880 may be a Xeon or Core processor from Intel of America or an Opteron processor from AMD of America, or may be other processor types that would be recognized by one of ordinary skill in the art. Alternatively, the CPU 1880 may be implemented on an FPGA, ASIC, PLD or using discrete logic circuits, as one of ordinary skill in the art would recognize. Further, CPU 1880 may be implemented as multiple processors cooperatively working in parallel to perform the instructions of the inventive processes described above.

The OTPS in FIG. 18 also includes a network controller 1883, such as an Intel Ethernet PRO network interface card from Intel Corporation of America, for interfacing with network 1895. As can be appreciated, the network 1895 can be a public network, such as the Internet, or a private network such as an LAN or WAN network, or any combination thereof and can also include PSTN or ISDN sub-networks. The network 1895 can also be wired, such as an Ethernet network, or can be wireless such as a cellular network including EDGE, 3G and 4G wireless cellular systems. The wireless network can also be WiFi, Bluetooth®, or any other wireless form of communication that is known.

The OTPS further includes a display controller 1884, such as a NVIDA GeForce GTX® or Quadro® graphics adaptor from NVIDIA Corporation of America for interfacing with display 1885, such as a Hewlett Packard HPL2445w® LCD monitor. A general purpose I/O interface 1886 interfaces with a keyboard and/or mouse 1887 as well as a touch screen panel 1888 on or separate from display 1885. General purpose I/O interface also connects to a variety of peripherals 1889 including printers and scanners, such as an OfficeJet® or DeskJet® from Hewlett Packard.

A sound controller 1890 is also provided in the OTPS, such as Sound Blaster X-Fi Titanium from Creative, to interface with speakers/microphone 1891 thereby providing sounds and/or music.

The general purpose storage controller 1892 connects the storage medium disk 1882 with communication bus 1893, which may be an ISA, EISA, VESA, PCI, or similar, for interconnecting all of the components of the OTPS. A description of the general features and functionality of the display 1885, keyboard and/or mouse 1887, as well as the display controller 1884, storage controller 1892, network controller 1883, sound controller 1890, and general purpose I/O interface 1886 is omitted herein for brevity as these features are known.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A method for generating an orthodontic treatment plan for at least one dental arch of a patient, comprising extracting control points of teeth of the at least one dental arch of the patient from received patient-related data, determining, based on the extracted control points, a target dental arch of the patient, calculating, based on the determined target dental arch of the patient, one or more teeth movement stages, and generating, by processing circuitry and based on the calculated one or more teeth movement stages, the orthodontic treatment plan for the at least one dental arch of the patient.

(2) The method according to (1), wherein the extracting the control points of each of the teeth of the at least one dental arch of the patient includes calculating isolines corresponding to a depth of a respective tooth in an xOz plane, generating a vertical axis of the respective tooth based on the calculated isolines, calculating isolines corresponding to a depth of the respective tooth in a plane orthogonal to the generated vertical axis, determining one or more dental features of the respective tooth, generating a horizontal axis of the respective tooth based on a subset of the determined one or more dental features of the respective tooth, and determining one or more contact points of the respective tooth.

(3) The method according to either (1) or (2), wherein the determining the one or more dental features of each respective tooth includes calculating at least one tooth cutting edge of the respective tooth, calculating at least one tooth tubercle of the respective tooth, and calculating at least one fissure of the respective tooth.

(4) The method according to any of (1) to (3), wherein the calculating the at least one fissure of the respective tooth includes determining a geometric area defined by the calculated at least one tooth tubercle of the respective tooth, dividing the geometric area into a plurality of geometric sub areas, and determining the at least one fissure of the respective tooth from coordinates of the plurality of geometric sub areas.

(5) The method according to any of (1) to (4), wherein the determining the target dental arch of the patient includes generating, accounting for dental collisions, a set of possible dental arches, and selecting, as the target dental arch, one of the set of possible dental arches that minimizes a difference with an ideal dental arch.

(6) The method according to any of (1) to (5), wherein the calculating the one or more teeth movement stages includes determining a quantity of the one or more teeth movement stages, calculating for each tooth at each teeth movement stage and accounting for dental collisions, a list of trajectories that satisfy a tooth movement, and selecting, for each tooth at each teeth movement stage, a trajectory of the list of trajectories that minimizes a penalty of transformation.

(7) The method according to any of (1) to (6), wherein the generated orthodontic treatment plan for the at least one dental arch of the patient includes a prescription for at least one dental aligner based on the selected trajectory for each tooth at each teeth movement stage.

(8) The method according to any of (1) to (7), wherein the extracting the control points of each of the teeth of the at least one dental arch of the patient includes applying a machine learning classifier to one or more images of the patient-related data, wherein the machine learning classifier is trained on a database of reference images of patients, each of the reference images of patients of the database being classified reference images of patients.

(9) An apparatus for generating an orthodontic treatment plan for at least one dental arch of a patient, comprising processing circuitry configured to extract control points for teeth of the at least one dental arch of the patient from received patient-related data, determine, based on the extracted control points, a target dental arch of the patient, calculate, based on the determined target dental arch of the patient, one or more teeth movement stages, and generate, based on the calculated one or more teeth movement stages, the orthodontic treatment plan for the at least one dental arch of the patient.

(10) The apparatus according to (9), wherein, in order to extract the control points for each of the teeth of the at least one dental arch of the patient, the processing circuitry is further configured to calculate isolines corresponding to a depth of a respective tooth in an xOz plane, generate a vertical axis of the respective tooth based on the calculated isolines, calculate isolines corresponding to a depth of the respective tooth in a plane orthogonal to the generated vertical axis, determine one or more dental features of the respective tooth, generate a horizontal axis of the respective tooth based on a subset of the determined one or more dental features of the respective tooth, and determine one or more contact points of the respective tooth.

(11) The apparatus according to either (9) or (10), wherein, in order to determine the one or more dental features of the respective tooth, the processing circuitry is further configured to calculate at least one tooth cutting edge of the respective tooth, calculate at least one tooth tubercle of the respective tooth, and calculate at least one fissure of the respective tooth.

(12) The apparatus according to any of (9) to (11), wherein, in order to determine the target dental arch of the patient, the processing circuitry is further configured to generate, accounting for dental collisions, a set of possible dental arches, and select, as the target dental arch, one of the set of possible dental arches that minimizes a difference with an ideal dental arch.

(13) The apparatus according to any of (9) to (12), wherein, in order to calculate the one or more teeth movement stages, the processing circuitry is further configured to determine a quantity of the one or more teeth movement stages, calculate, for each tooth at each teeth movement stage and accounting for dental collisions, a list of trajectories that satisfy a tooth movement, and select, for each tooth at each teeth movement stage, a trajectory of the list of trajectories that minimizes a penalty of transformation.

(14) The apparatus according to any of (9) to (13), wherein, in order to extract the control points for each of the teeth of the at least one dental arch of the patient, the processing circuitry is further configured to apply a machine learning classifier to one or more images of the patient-related data, wherein the machine learning classifier is trained on a database of reference images of patients, each of the reference images of patients of the database being classified reference images of patients.

(15) A non-transitory computer-readable storage medium storing computer-readable instructions that, when executed by a computer, cause the computer to perform a method of generating an orthodontic treatment plan for at least one dental arch of a patient, comprising extracting control points of teeth of the at least one dental arch of the patient from received patient-related data, determining, based on the extracted control points, a target dental arch of the patient, calculating, based on the determined target dental arch of the patient, one or more teeth movement stages, and generating, based on the calculated one or more teeth movement stages, the orthodontic treatment plan for the at least one dental arch of the patient.

(16) The non-transitory computer-readable storage medium according to (15), wherein the extracting the control points for each of the teeth of the at least one dental arch of the patient includes calculating isolines corresponding to a depth of a respective tooth in an xOz plane, generating a vertical axis of the respective tooth based on the calculated isolines, calculating isolines corresponding to a depth of the respective tooth in a plane orthogonal to the generated vertical axis, determining one or more dental features of the respective tooth, generating a horizontal axis of the respective tooth based on a subset of the determined one or more dental features of the respective tooth, and determining one or more contact points of the respective tooth.

(17) The non-transitory computer-readable storage medium according to either (15) or (16), wherein the determining the one or more dental features of the respective tooth includes calculating at least one tooth cutting edge of the respective tooth, calculating at least one tooth tubercle of the respective tooth, and calculating at least one fissure of the respective tooth.

(18) The non-transitory computer-readable storage medium according to any of (15) to (17), wherein the determining the target dental arch of the patient includes generating, accounting for dental collisions, a set of possible dental arches, and selecting, as the target dental arch, one of the set of possible dental arches that minimizes a difference with an ideal dental arch.

(19) The non-transitory computer-readable storage medium according to any of (15) to (18), wherein the calculating the one or more teeth movement stages includes determining a quantity of the one or more teeth movement stages, calculating, for each tooth at each teeth movement stage and accounting for dental collisions, a list of trajectories that satisfy a tooth movement, and selecting, for each tooth at each teeth movement stage, a trajectory of the list of trajectories that minimizes a penalty of transformation.

(20) The non-transitory computer-readable storage medium according to any of (15) to (19), wherein the extracting the control points for each of the teeth of the at least one dental arch of the patient includes applying a machine learning classifier to one or more images of the patient-related data, wherein the machine learning classifier is trained on a database of reference images of patients, each of the reference images of patients of the database being classified reference images of patients.

Thus, the foregoing discussion discloses and describes merely exemplary embodiments of the present invention. As will be understood by those skilled in the art, the present invention may be embodied in other specific forms without departing from the spirit or essential characteristics thereof. Numerous modification and variations on the present invention are possible in light of the above teachings. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

All publications, patent applications, patents, and other references mentioned herein are incorporated by reference in their entirety. Further, the materials, methods, and examples are illustrative only and are not intended to be limiting, unless otherwise specified.

The invention claimed is:

1. A method for generating an orthodontic treatment plan for at least one dental arch of a patient, comprising:
    extracting control points of teeth of the at least one dental arch of the patient from received patient-related data, including:
        applying a machine learning classifier to one or more images of the patient-related data, the machine learning classifier being trained on a database of reference images of patients and each of the reference images of patients of the database being classified reference images of patients;
    determining, based on the extracted control points, a target dental arch of the patient that is different from the at least one dental arch, including:
        generating, accounting for dental collisions, a set of possible dental arches that are each different from the at least one dental arch, and
        selecting, as the target dental arch, one of the set of possible dental arches that minimizes a difference between the one of the set of possible dental arches and an ideal dental arch;
    calculating, based on the determined target dental arch of the patient, one or more teeth movement stages, the one or more teeth movement stages representing a stage of movement of at least one tooth from a state in the at least one dental arch to a state in the target dental arch; and
    generating, by processing circuitry and based on the calculated one or more teeth movement stages, the orthodontic treatment plan for the at least one dental arch of the patient, the generated orthodontic treatment plan for the at least one dental arch of the patient including information required to produce at least one dental aligner based on the selected trajectory for each tooth at each teeth movement stage.

2. The method according to claim 1, wherein the extracting the control points of each of the teeth of the at least one dental arch of the patient includes:
    calculating isolines corresponding to a depth along a y direction of a respective tooth in an xOz plane,
    generating a vertical axis of the respective tooth based on the calculated isolines,
    calculating isolines corresponding to a depth along the vertical axis of the respective tooth in a plane orthogonal to the generated vertical axis,
    determining one or more dental features of the respective tooth based upon the isolines corresponding to the depth along the vertical axis,
    generating a horizontal axis of the respective tooth based on a subset of the determined one or more dental features of the respective tooth, and
    determining one or more contact points of the respective tooth based upon the horizontal axis.

3. The method according to claim 2, wherein the determining the one or more dental features of each respective tooth includes one or more of:
    calculating at least one tooth cutting edge of the respective tooth,
    calculating at least one tooth tubercle of the respective tooth, and
    calculating at least one fissure of the respective tooth.

4. The method according to claim 3, wherein the calculating the at least one fissure of the respective tooth includes:
    determining a geometric area defined by the calculated at least one tooth tubercle of the respective tooth,
    dividing the geometric area into a plurality of geometric sub areas, and
    determining the at least one fissure of the respective tooth from coordinates of the plurality of geometric sub areas.

5. The method according to claim 1, wherein the calculating the one or more teeth movement stages includes:
    determining a quantity of the one or more teeth movement stages,
    calculating for each tooth at each teeth movement stage and accounting for dental collisions, a list of trajectories that satisfy a tooth movement, and
    selecting, for each tooth at each teeth movement stage, a trajectory of the list of trajectories that minimizes a penalty of transformation.

6. An apparatus for generating an orthodontic treatment plan for at least one dental arch of a patient, comprising:
    processing circuitry configured to
    extract control points for teeth of the at least one dental arch of the patient from received patient-related data, including:
        applying a machine learning classifier to one or more images of the patient-related data, the machine learning classifier being trained on a database of reference images of patients and each of the reference images of patients of the database being classified reference images of patients,
    determine, based on the extracted control points, a target dental arch of the patient that is different from the at least one dental arch, including:
        generate, accounting for dental collisions, a set of possible dental arches that are each different from the at least one dental arch, and
        select, as the target dental arch, one of the set of possible dental arches that minimizes a difference between the one of the set of possible dental arches and an ideal dental arch,
    calculate, based on the determined target dental arch of the patient, one or more teeth movement stages, the one or more teeth movement stages representing a stage of movement of at least one tooth from a state in the at least one dental arch to a state in the target dental arch, and
    generate, based on the calculated one or more teeth movement stages, the orthodontic treatment plan for the at least one dental arch of the patient, the generated orthodontic treatment plan for the at least one dental arch of the patient including information required to produce at least one dental aligner based on the selected trajectory for each tooth at each teeth movement stage.

7. The apparatus according to claim 6, wherein, in order to extract the control points for each of the teeth of the at least one dental arch of the patient, the processing circuitry is further configured to
    calculate isolines corresponding to a depth along a y direction of a respective tooth in an xOz plane,
    generate a vertical axis of the respective tooth based on the calculated isolines,
    calculate isolines corresponding to a depth along the vertical axis of the respective tooth in a plane orthogonal to the generated vertical axis,
    determine one or more dental features of the respective tooth based upon the isolines corresponding to the depth along the vertical axis,
    generate a horizontal axis of the respective tooth based on a subset of the determined one or more dental features of the respective tooth, and determine one or more contact points of the respective tooth based upon the horizontal axis.

8. The apparatus according to claim 7, wherein, in order to determine the one or more dental features of the respective tooth, the processing circuitry is further configured to:
calculate at least one tooth cutting edge of the respective tooth,
calculate at least one tooth tubercle of the respective tooth, and/or
calculate at least one fissure of the respective tooth.

9. The apparatus according to claim 6, wherein, in order to calculate the one or more teeth movement stages, the processing circuitry is further configured to:
determine a quantity of the one or more teeth movement stages,
calculate, for each tooth at each teeth movement stage and accounting for dental collisions, a list of trajectories that satisfy a tooth movement, and
select, for each tooth at each teeth movement stage, a trajectory of the list of trajectories that minimizes a penalty of transformation.

10. A non-transitory computer-readable storage medium storing computer-readable instructions that, when executed by a computer, cause the computer to perform a method of generating an orthodontic treatment plan for at least one dental arch of a patient, the method comprising:
extracting control points of teeth of the at least one dental arch of the patient from received patient-related data, including:
applying a machine learning classifier to one or more images of the patient-related data, the machine learning classifier being trained on a database of reference images of patients and each of the reference images of patients of the database being classified reference images of patients;
determining, based on the extracted control points, a target dental arch of the patient that is different from the at least one dental arch, including:
generating, accounting for dental collisions, a set of possible dental arches that are each different from the at least one dental arch, and
selecting, as the target dental arch, one of the set of possible dental arches that minimizes a difference between the one of the set of possible dental arches and an ideal dental arch;
calculating, based on the determined target dental arch of the patient, one or more teeth movement stages, the one or more teeth movement stages representing a stage of movement of at least one tooth from a state in the at least one dental arch to a state in the target dental arch; and
generating, based on the calculated one or more teeth movement stages, the orthodontic treatment plan for the at least one dental arch of the patient, the generated orthodontic treatment plan for the at least one dental arch of the patient including information required to produce at least one dental aligner based on the selected trajectory for each tooth at each teeth movement stage.

11. The non-transitory computer-readable storage medium according to claim 10, wherein the extracting the control points for each of the teeth of the at least one dental arch of the patient includes
calculating isolines corresponding to a depth along a y direction of a respective tooth in an xOz plane,
generating a vertical axis of the respective tooth based on the calculated isolines,
calculating isolines corresponding to a depth along the vertical axis of the respective tooth in a plane orthogonal to the generated vertical axis,
determining one or more dental features of the respective tooth based upon the isolines corresponding to the depth along the vertical axis,
generating a horizontal axis of the respective tooth based on a subset of the determined one or more dental features of the respective tooth, and
determining one or more contact points of the respective tooth based upon the horizontal axis.

12. The non-transitory computer-readable storage medium according to claim 11, wherein the determining the one or more dental features of the respective tooth includes one or more of:
calculating at least one tooth cutting edge of the respective tooth,
calculating at least one tooth tubercle of the respective tooth, and
calculating at least one fissure of the respective tooth.

13. The non-transitory computer-readable storage medium according to claim 10, wherein the calculating the one or more teeth movement stages includes:
determining a quantity of the one or more teeth movement stages,
calculating, for each tooth at each teeth movement stage and accounting for dental collisions, a list of trajectories that satisfy a tooth movement, and
selecting, for each tooth at each teeth movement stage, a trajectory of the list of trajectories that minimizes a penalty of transformation.

* * * * *